(12) United States Patent
Taylor et al.

(10) Patent No.: US 7,863,419 B2
(45) Date of Patent: Jan. 4, 2011

(54) ANTIBODIES HAVING ALTERED EFFECTOR FUNCTION AND METHODS FOR MAKING THE SAME

(75) Inventors: Frederick R. Taylor, Milton, MA (US); Ellen Garber, Cambridge, MA (US)

(73) Assignee: Biogen Idec MA Inc., Cambridge, MA (US)

( * ) Notice: Subject to any disclaimer, the term of this patent is extended or adjusted under 35 U.S.C. 154(b) by 363 days.

(21) Appl. No.: 11/360,938

(22) Filed: Feb. 22, 2006

(65) Prior Publication Data

US 2007/0048300 A1 Mar. 1, 2007

Related U.S. Application Data

(63) Continuation of application No. PCT/US2004/027476, filed on Aug. 23, 2004.

(60) Provisional application No. 60/497,193, filed on Aug. 22, 2003.

(51) Int. Cl.
*C07K 16/00* (2006.01)
*C07K 16/46* (2006.01)

(52) U.S. Cl. .................... 530/350; 530/387.3

(58) Field of Classification Search ........................ None
See application file for complete search history.

(56) References Cited

U.S. PATENT DOCUMENTS

| | | | |
|---|---|---|---|
| 5,585,097 A | 12/1996 | Bolt et al. | |
| 5,624,821 A | 4/1997 | Winter et al. | |
| 5,648,260 A | 7/1997 | Winter et al. | |
| 5,714,350 A | 2/1998 | Co et al. | |
| 6,165,745 A | 12/2000 | Ward et al. | |
| 6,194,551 B1 | 2/2001 | Idusogie et al. | |
| 6,218,149 B1 | 4/2001 | Morrison et al. | |
| 6,277,375 B1 | 8/2001 | Ward | |
| 6,284,536 B1 | 9/2001 | Morrison et al. | |
| 6,350,861 B1 | 2/2002 | Co et al. | |
| 6,528,624 B1 | 3/2003 | Idusogie et al. | |
| 6,538,124 B1 | 3/2003 | Idusogie et al. | |
| 6,720,165 B2 | 4/2004 | Nock et al. | |
| 6,737,056 B1 | 5/2004 | Presta | |
| 6,821,505 B2 | 11/2004 | Ward | |
| 6,933,368 B2 | 8/2005 | Co et al. | |
| 6,979,553 B2 | 12/2005 | Farinas et al. | |
| 7,083,784 B2 | 8/2006 | Dall'Acqua et al. | |
| 7,183,387 B1 | 2/2007 | Presta | |
| 7,217,797 B2 | 5/2007 | Hinton et al. | |
| 7,217,798 B2 | 5/2007 | Hinton et al. | |
| 7,247,302 B1 | 7/2007 | Rosok et al. | |
| 7,297,775 B2 | 11/2007 | Idusogie et al. | |
| 7,317,091 B2 | 1/2008 | Lazar et al. | |
| 7,332,581 B2 | 2/2008 | Presta | |
| 7,335,742 B2 | 2/2008 | Presta | |
| 7,351,803 B2 | 4/2008 | Johnson et al. | |
| 7,355,008 B2 | 4/2008 | Stavenhagen et al. | |
| 2002/0131968 A1 | 9/2002 | Waldmann et al. | |
| 2002/0147312 A1 | 10/2002 | O'Keefe et al. | |
| 2002/0193573 A1 | 12/2002 | Nock et al. | |
| 2003/0026692 A1 | 2/2003 | Lutz | |
| 2003/0073164 A1 | 4/2003 | Simmons et al. | |
| 2003/0158389 A1 | 8/2003 | Idusogie et al. | |
| 2004/0006216 A1 | 1/2004 | Waldmann et al. | |
| 2004/0010124 A1 | 1/2004 | Johnson et al. | |
| 2004/0091957 A1 | 5/2004 | Nock et al. | |
| 2004/0132101 A1* | 7/2004 | Lazar et al. | 435/7.1 |
| 2004/0191244 A1 | 9/2004 | Presta | |
| 2004/0228856 A1 | 11/2004 | Presta | |
| 2005/0054832 A1 | 3/2005 | Lazar et al. | |
| 2005/0064514 A1 | 3/2005 | Stavenhagen et al. | |
| 2005/0118174 A1 | 6/2005 | Presta | |
| 2005/0170464 A1 | 8/2005 | Simmons et al. | |
| 2005/0215768 A1 | 9/2005 | Armour et al. | |
| 2005/0233382 A1 | 10/2005 | Presta | |
| 2005/0244403 A1 | 11/2005 | Lazar et al. | |
| 2006/0024298 A1 | 2/2006 | Lazar et al. | |
| 2006/0160996 A9 | 7/2006 | Lazar et al. | |
| 2006/0193856 A1 | 8/2006 | Taylor et al. | |
| 2006/0275283 A1* | 12/2006 | van Vlijmen et al. | 424/130.1 |
| 2007/0092516 A1 | 4/2007 | Waldmann et al. | |
| 2007/0202098 A1 | 8/2007 | Lazar et al. | |
| 2007/0219133 A1 | 9/2007 | Lazar et al. | |
| 2007/0224189 A1 | 9/2007 | Lazar et al. | |
| 2007/0224192 A1 | 9/2007 | Lazar et al. | |
| 2007/0237767 A1 | 10/2007 | Lazar et al. | |

(Continued)

FOREIGN PATENT DOCUMENTS

EP 0255694 A1 2/1988

(Continued)

OTHER PUBLICATIONS

Attwood T. Science 2000; 290:471-47.*

(Continued)

*Primary Examiner*—Ilia Ouspenski
(74) *Attorney, Agent, or Firm*—Lahive & Cockfield, LLP; Megan E. Williams

(57) ABSTRACT

The invention provides a method of producing aglycosylated Fc-containing polypeptides, such as antibodies, having desired effector function. The invention also provides aglycosylated antibodies produced according to the method as well as methods of using such antibodies as therapeutics.

88 Claims, 15 Drawing Sheets

U.S. PATENT DOCUMENTS

| | | |
|---|---|---|
| 2007/0238665 A1 | 10/2007 | Lazar et al. |
| 2007/0243188 A1 | 10/2007 | Lazar et al. |
| 2007/0244303 A1 | 10/2007 | Johnson et al. |
| 2007/0248602 A1 | 10/2007 | Lazar et al. |
| 2007/0248603 A1 | 10/2007 | Lazar et al. |
| 2008/0050371 A1 | 2/2008 | Johnson et al. |
| 2008/0051563 A1 | 2/2008 | Lazar et al. |
| 2008/0206867 A1 | 8/2008 | Desjarlais et al. |
| 2009/0010920 A1 | 1/2009 | Lazar et al. |
| 2009/0068175 A1 | 3/2009 | Lazar et al. |

FOREIGN PATENT DOCUMENTS

| | | |
|---|---|---|
| WO | WO-88/07089 A1 | 9/1988 |
| WO | WO-89/07142 A1 | 8/1989 |
| WO | WO-93/19196 A1 | 9/1993 |
| WO | WO-93/22332 A1 | 11/1993 |
| WO | WO-94/28027 A1 | 12/1994 |
| WO | WO-94/29351 A2 | 12/1994 |
| WO | WO-97/34631 A1 | 9/1997 |
| WO | WO-98/05787 A1 | 2/1998 |
| WO | WO-98/23289 A1 | 6/1998 |
| WO | WO-98/47531 A2 | 10/1998 |
| WO | WO-99/22764 A1 | 5/1999 |
| WO | WO-99/51642 A1 | 10/1999 |
| WO | WO-99/54484 A1 | 10/1999 |
| WO | WO-99/58572 A1 | 11/1999 |
| WO | WO-00/05268 A1 | 2/2000 |
| WO | WO-00/42072 A2 | 7/2000 |
| WO | WO-02/060919 A2 | 8/2002 |
| WO | WO-02/062850 A2 | 8/2002 |
| WO | WO-02/066514 A2 | 8/2002 |
| WO | WO-02/079232 A2 | 10/2002 |
| WO | WO-03/001870 A2 | 1/2003 |
| WO | WO-03/026692 A2 | 4/2003 |
| WO | WO-03/035835 A2 | 5/2003 |
| WO | WO-03/059282 A2 | 7/2003 |
| WO | WO-03/074679 A2 | 9/2003 |
| WO | WO-03/101485 A1 | 12/2003 |
| WO | WO-2004/029207 A2 | 4/2004 |
| WO | WO-2004/035752 A2 | 4/2004 |
| WO | WO-2004/063351 A2 | 7/2004 |
| WO | WO-2004/063963 A2 | 7/2004 |
| WO | WO-2004/074455 A2 | 9/2004 |
| WO | WO-2004/074499 A2 | 9/2004 |
| WO | WO-2004/099249 A2 | 11/2004 |
| WO | WO-2005/003175 A2 | 1/2005 |
| WO | WO-2005/018572 A2 | 3/2005 |
| WO | WO-2005/040217 A2 | 5/2005 |
| WO | WO-2005/056606 A2 | 6/2005 |
| WO | WO-2005/056759 A2 | 6/2005 |
| WO | WO-2005/070963 A1 | 8/2005 |
| WO | WO-2005/077981 A2 | 8/2005 |
| WO | WO-2005/115452 A2 | 12/2005 |
| WO | WO-2006/019447 A1 | 2/2006 |
| WO | WO-2006/020114 A2 | 2/2006 |
| WO | WO-2006/031370 A2 | 3/2006 |
| WO | WO-2006/033702 A2 | 3/2006 |
| WO | WO-2007/059332 A2 | 5/2007 |
| WO | 2007/100289 A2 | 9/2007 |

OTHER PUBLICATIONS

Skolnick et al., Trends in Biotech. 2000; 18(1):34-39.*

Notification of Transmittal of the International Search Report and the Written Opinion of the International Searching Authority, or the Declaration for Application No. PCT/US2004/27476, dated Jan. 20, 2006.

Shields, Robert L. et al., "High Resolution Mapping of the Binding Site on Human IgG1 for FcγRI, FcγRII, FcγRIII, and FcRn and Design of IgG1 Variants with Improved Binding to the FcγR," *The Journal of Biological Chemistry*, vol. 276(9):6591-6604 (2001).

Sondermann, Peter et al., "The 3.2-Å crystal structure of the human IgG1 Fc fragment-FcγRIII complex," *Nature*, vol. 406:267-273 (2000).

Tao, Mi-Hua et al., "Studies of Aglycosylated Chimeric Mouse-Human IgG, Role of Carbohydrate in the Structure and Effector Functions Mediated by the Human IgG Constant Region," *The Journal of Immunology*, vol. 143(8):2595-2601 (1989).

Supplementary European Search Report for Application No. 04782045.1, dated May 7, 2009.

Armour, Kathryn L. et al., "Differential binding to human FcγRIIa and FcγRIIb receptors by human IgG wildtype and mutant antibodies," Molecular Immunology, vol. 40:585-593 (2003).

Armour, Kathryn L. et al., "Recombinant human IgG molecules lacking Fcγ receptor I binding and monocyte triggering activities," *Eur. J. Immunol.*, vol. 29:2613-2624 (1999).

Bastida-Corcuera, F.D. et al., "Differential complement activation by bovine IgG2 allotypes," *Veterinary Immunology and Immunopathology*, vol. 71:115-123 (1999).

Boyd, P.N. et al., "The effect of the removal of sialic acid, galactose and total carbohydrate on the functional activity of campath-1H," *Molecular Immunology*, vol. 32(17/18):1311-1318 (1995).

Brekke, Ole Henrik et al., "Human IgG isotype-specific amino acid residues affecting complement-mediated cell lysis and phagocytosis," *Eur. J. Immunol.*, vol. 24:2542-2547 (1994).

Burton, Dennis R., "Immunoglobulin G: Functional Sites," *Molecular Immunology*, vol. 22(3):161-206 (1985).

Burton, D.R. et al., "The C1q receptor site on immunoglobulin G," *Nature*, vol. 288:338-344 (1980).

Canfield, Stephen M. et al., "The Binding Affinity of Human IgG for its High Affinity Fc Receptor Is Determined by Multiple Amino Acids in the CH2 Domain and Is Modulated by the Hinge Region," *J. Exp. Med.*, vol. 173:1483-1491 (1991).

Caron, Philip C. et al., "Engineered Humanized Dimeric Forms of IgG Are More Effective Antibodies," *J. Exp. Med.*, vol. 176:1191-1195 (1992).

Chan, Lisa A. et al., "Variable region domain exchange in human IgGs promotes antibody complex formation with accompanying structural changes and altered effector functions," *Molecular Immunology*, vol. 41:527-538 (2004).

Chappel, M. Suzanne et al., "Identification of the Fcγ receptor class I binding site in human IgG through the use of recombinant IgG1/IgG2 hybrid and point-mutated antibodies," *Proc. Natl. Acad. Sci. USA*, vol. 88:9036-9040 (1991).

Chirino, Arthur J. et al., "Minimizing the immunogenicity of protein therapeutics," *Drug Discovery Today*, vol. 9(2):82-90 (2004).

Cole, Michael S. et al., "HuM291, A Humanized Anti-CD3 Antibody, is Immunosuppressive to T Cells While Exhibiting Reduced Mitogenicity in Vitro," *Transplantation*, vol. 68(4):563-571 (1999).

Cole, Michael S. et al., "Human IgG2 Variants of Chimeric Anti-CD3 Are Nonmitogenic to T Cells," *The Journal of Immunology*, vol. 159:3613-3621 (1997).

Daeron, Marc, "Fc Receptor Biology," *Annu. Rev. Immunol.*, vol. 15:203-234 (1997).

Dahiyat, Bassil I. et al., "Protein design automation," *Protein Science*, vol. 5:895-903 (1996).

Dall'Acqua, William F. et al., "Modulation of the Effector Functions of a Human IgG1 through Engineering of Its Hinge Region," *The Journal of Immunology*, vol. 177:1129-1138 (2006).

Dorai, Haimanti et al., "Aglycosylated Chimeric Mouse/Human IgG1 Antibody Retains Some Effector Function," *Hybridoma*, vol. 10(2):211-217 (1991).

Duncan, Alexander R. et al., "Localization of the binding site for the human high-affinity Fc receptor on IgG," *Nature*, vol. 332:563-564 (1988).

Duncan, Alexander R. et al., "The binding site for C1q on IgG," *Nature*, vol. 332:738-740 (1988).

Elster, Eric A. et al., "Treatment with the Humanized CD154-Specific Monoclonal Antibody, hu5C8, Prevents Acute Rejection of Primary Skin Allografts in Nonhuman Primates," *Transplantation*, vol. 72(9):1473-1478 (2001).

Friend, P.J. et al., "Phase I Study of an Engineered Aglycosylated Humanized CD3 Antibody in Renal Transplant Rejection," *Transplantation*, vol. 68(11):1632-1637 (1999).

Gergely, J. et al., "Fc receptors on lymphocytes and K cells," *Biochemical Society Transactions*, vol. 12(5):739-743 (1984).

Gillies, Stephen D. et al., "Improving the Efficacy of Antibody-Interleukin 2 Fusion Proteins by Reducing Their Interaction with Fc Receptors," *Cancer Research*, vol. 59:2159-2166 (1999).

Graddis, T.J. et al., "Designing Proteins That Work Using Recombinant Technologies," *Current Pharmaceutical Biotechnology*, vol. 3:285-297 (2002).

Hand, Patricia Horan et al., "Comparative biological properties of a recombinant chimeric anti-carcinoma mAb and a recombinant aglycosylated variant," *Cancer Immunol. Immunother.*, vol. 35:165-174 (1992).

Hayes, Robert J. et al., "Combining computational and experimental screening for rapid optimization of protein properties," *PNAS*, vol. 99(25):15926-15931 (2002).

Hobbs, S.M. et al., "Interaction of Aglycosyl Immunoglobulins with the IgG Fc Transport Receptor from Neonatal Rat Gut: Comparison of Deglycosylation by Tunicamycin Treatment and Genetic Engineering," *Molecular Immunology*, vol. 29(7/8):949-956 (1992).

Hsu, Tsu-An et al., "Differential N-Glycan Patterns of Secreted and Intracellular IgG Produced in *Trichoplusia ni* Cells," *The Journal of Biological Chemistry*, vol. 272(14):9062-9070 (1997).

Idusogie, Esohe E. et al., "Mapping of the C1q Binding Site on Rituxan, a Chimeric Antibody with a Human IgG1 Fc," *The Journal of Immunology*, vol. 164:4178-4184 (2000).

Isaacs, John D. et al., "Therapy with Monoclonal Antibodies, An in Vivo Model for the Assessment of Therapeutic Potential," *The Journal of Immunology*, vol. 148(10):3062-3071 (1992).

Jefferis, R. et al., "Glycosylation of antibody molecules: structural and functional significance," *Chem. Immunol.*, vol. 65:111-128 (1997).

Kato, K. et al., "Analysis of IgG-FcγR Interactions in Solution: Mapping of the FcγR Binding Site and Evidence for a Conformational Change Occuring in the Fc Region," *Immunology, Letters*, vol. 73(2-3) No. 409 (2000).

Klein, Michel et al., "Expression of biological effector functions by immunoglobulin G molecules lacking the hinge region," *Proc. Natl. Acad. Sci. USA*, vol. 78(1):524-528 (1981).

Kunkel, Thomas A., "Rapid and efficient site-specific mutageneis without phenotypic selection," *Proc. Natl. Acad. Sci. USA*, vol. 82:488-492 (1985).

Lazar, Greg A. et al., "Engineered antibody Fc variants with enhanced effector function," *PNAS*, vol. 103(11):4005-4010 (2006).

Leader, K.A. et al., "Functional interactions of aglycosylated monoclonal anti-D with FcγRI+ and FcyRIII+ cells," *Immunology*, vol. 72:481-485 (1991).

Leatherbarrow, Robin J. et al., "Effector Functions of a Monoclonal Aglycosylated Mouse IgG2a: Binding and Activation of Complement Component C1 and Interaction with Human Monocyte Fc Receptor," *Molecular Immunology*, vol. 22(4):407-415 (1985).

Leatherbarrow, Robin J. et al., "The effect of aglycosylation on the binding of mouse IgG to staphylococcal protein A," *FEBS*, vol. 164(2):227-230 (1983).

Liu, Alvin Y. et al., "Production of a Mouse-human Chimeric Monoclonal Antibody to CD20 with Potent Fc-Dependent Biologic Activity," *The Journal of Immunology*, vol. 139(10):3521-3526 (1987).

Lund John et al., "A Protein Structural Change in Aglycosylated IgG3 Correlates with Loss of huFcγR1 and huFcγRIII Binding and/or Activation," *Molecular Immunology*, vol. 27(11):1145-1153 (1990).

Lund John et al., "Human FcγRI and FcγRII Interact with Distinct but Overlapping Sites on Human IgG," *The Journal of Immunology*, vol. 147(8):2657-2662 (1991).

Morrison, Sherie L. et al., "Variable Region Domain Exchange Influences the Functional Properties of IgG," *The Journal of Immunology*, vol. 160:2802-2808 (1998).

Marzocchi-Machado, C.M. et al., "The Influence of Antibody Functional Affinity on the Effector Functions Involved in the Clearance of Circulating Immune Complexes Anti-BSA IgG/BSA," *Immunological Investigations*, vol. 28(2&3):89-101 (1999).

Mueller, John P. et al., "Humanized Porcine VCAM-Specific Monoclonal Antibodies with Chimeric IgG2/G4 Constant Regions Block Human Leukocyte Binding to Porcine Endothelial Cells," *Molecular Immunology*, vol. 34(6):441-452 (1997).

Natsume, Akito et al., "Engineered Antibodies of IgG1/IgG3 Mixed Isotype with Enhanced Cytotoxic Activities," *Cancer Research*, vol. 68(10):3863-3872 (2008).

Newkirk, M.M. et al., "Differential clearance of glycoforms of IgG in normal and autoimmune-prone mice," *Clin. Exp. Immunol.*, vol. 106:259-264 (1996).

Nose, Masato et al., "Biological significance of carbohydrate chains on monoclonal antibodies," *Proc. Natl. Acad. Sci. USA*, vol. 80:6632-6636 (1983).

Patel, Thakor P. et al., "Different culture methods lead to differences in glycosylation of a murine IgG monoclonal antibody," *Biochem. J.*, vol. 285:839-845 (1992).

Pendley, Charles et al., "Immunogenicity of therapeutic monoclonal antibodies," *Current Opinion in Molecular Therapeutics*, vol. 5(2):172-179 (2003).

Pound, John D. et al., "Aglycosylated Chimaeric Human IgG3 Can Trigger the Human Phagocyte Respiratory Burst," *Molecular Immunology*, vol. 30(3):233-241 (1993).

Radaev, Sergei et al., "The Structure of a Human Type III Fcγ Receptor in Complex with Fc," *The Journal of Biological Chemistry*, vol. 276(19):16469-16477 (2001).

Raju, T. Shantha, "Glycosylation Variations with Expression Systems and Their Impact on Biological Activity of Therapeutic Immunoglobulins," *BioProcess International*, 44-53 (2003).

Raju, T. Shantha et al., "Species-specific variation in glycosylation of IgG: evidence for the species-specific sialylation and branch-specific galactosylation and importance for engineering recombinant glycoprotein therapeutics," *Glycobiology*, vol. 10(5):477-486 (2000).

Ravetch, Jeffrey V. et al., "Fc Receptors," *Annu. Rev. Immunol.*, vol. 9:457-492 (1991).

Sármay, G. et al., "Ligand Inhibition Studies on the Role of Fc Receptors in Antibody-Dependent Cell-mediated Cytotoxicity," *Molecular Immunology*, vol. 21(1):43-51 (1984).

Shitara, Kenya et al., "A new vector for the high level expression of chimeric antibodies in myeloma cells," *Journal of Immunological Methods*, vol. 167:271-278 (1994).

Shields, Robert L. et al., "Lack of Fucose on Human IgG1 N-Linked Oligosaccharide Improves Binding to Human FcγRIII and Antibody-dependent Cellular Toxicity," *The Journal of Biological Chemistry*, vol. 277(30):26733-26740 (2002).

Shinkawa, Toyohide et al., "The Absence of Fucose but Not the Presence of Galactose or Bisecting N-Acetylglucosamine of Human IgG1 Complex-type Oligosaccharides Shows the Critical Role of Enhancing Antibody-dependent Cellular Cytotoxicity," *The Journal of Biological Chemistry*, vol. 278(5):3466-3473 (2003).

Shopes, Bob, "A Genetically Engineered Human IgG Mutant with Enhanced Cytolytic Activity," *The Journal of Immunology*, vol. 148(9):2918-2922 (1992).

Simmons, Laura C. et al., "Expression of full-length immunoglobulins in *Escherichia coli*: rapid and efficient production of aglycosylated antibodies," *Journal of Immunological Methods*, vol. 263:133-147 (2002).

Sondermann, P. et al., "Mediation and Modulation of Antibody Function," *Biochemical Society Transactions*, vol. 30:481-486 (2002).

Tamm, Anu et al., "IgG Binding Sites on Human Fcγ Receptors," *Intern. Rev. Immunol.*, vol. 16:57-85 (1997).

Tao, Mi-Hua et al., "Structural Features of Human Immunoglobulin G that Determine Isotype-specific Differences in Complement Activation," *J. Exp. Med.*, vol. 178:661-667 (1993).

Trebak, Mohamed et al., "Efficient laboratory-scale production of monoclonal antibodies using membrane-based high-density cell culture technology," *Journal of Immunological Methods*, vol. 230:59-70 (1999).

Umaña, Pablo et al., "Engineered glycoforrns of an antineuroblastoma IgG1 with optimized antibody-dependent cellular cytotoxic activity," *Nature Biotechnology*, vol. 17:176-180 (1999).

Waldmann, Herman, "The new immunosuppressive: just kill the T cell," *Nature Medicine*, vol. 9(10):1259-1260 (2003).

Valerius, Thomas et al., "FcαRl (CD89) as a Novel Trigger Molecule for Bispecific Antibody Therapy," *Blood*, vol. 90(11):4485-4492 (1997).

Vitetta, Ellen S. et al., "Considering Therapeutic Antibodies," *Science*, vol. 313:308-309 (2006).

Walker, Matthew R. et al., "Aglycosylation of human IgG1 and IgG3 monoclonal antibodies can eliminate recognition by human cells expressing FcγRl and/or RcγRll receptors," *Biochem. J.*, vol. 259:347-353 (1989).

Ward, E.S. et al., "The effector functions of immunoglobulins: implications for therapy," *Therapeutic Immunology*, vol. 2:77-94 (1995).

Williams, Ralph C. Jr. et al., "Studies of Biologic and Serologic Activities of Rabbit-IgG Antibody Depleted of Carbohydrate Residues," *The Journal of Immunology*, vol. 111(6):1690-1698 (1973).

W.H.O., "Review of the notation for the allotypic and related markers of human immunoglobulins," *Eur. J. Immunol.*, vol. 6:599-601 (1976).

W.H.O., "Review of the Notation for the Allotypic and Related Markers for Human Immunoglobulins," *Journal of Immunogenetics*, vol. 3:357-362 (1976).

Winkelhake, Jeffrey L. et al., "Aglycosylantibody, Effects of Exoglycosidase Treatments on Autochthonous Antibody Survival Time in the Circulation," *The Journal of Biological Chemistry*, vol. 251(4):1074-1080 (1976).

Woof, J.M. et al., "Localisation of the Monocyte-binding Region of Human Immunoglobulin G," *Molecular Immunology*, vol. 23(3):319-330 (1986).

Wright, Ann et al., "Effect of Altered CH2-associated Carbohydrate Structure on the Functional Properties and in Vivo Fate of Chimeric Mouse-Human Immunoglobulin G1," *J. Exp. Med.*, vol. 180:1087-1096 (1994).

Yamane-Ohnuki, Naoko et al., "Establishment of FUT8 Knockout Chinese Hamster Ovary Cells: An Ideal Host Cell Line for Producing Completely Defucosylated Antibodies With Enhanced Antibody-Dependent Cellular Cytotoxicity," *Biotechnology and Bioengineering*, vol. 87(5):614-622 (2004).

European Office Action for Application No. 04782045, dated Dec. 30, 2009.

* cited by examiner

Activated U937 Cells on CHO-CD40L

CD16 Bridging to CHO-CD40L

Bridging to activated U937 cells

Bridging to CD16 Jurkats

Aglycosylated Antibodies Have Reduced C1q Binding

ANTIBODIES HAVING ALTERED EFFECTOR FUNCTION AND METHODS FOR MAKING THE SAME

RELATED INFORMATION

The application is a continuation of co-pending International Application No. PCT/US2004/027476, filed Aug. 23, 2004, which, in turn, claims priority to U.S. provisional patent application No. 60/497,193, filed on Aug. 22, 2003. The entire contents of the above-identified applications are hereby incorporated by reference in their entirety.

The contents of any patents, patent applications, and references cited throughout this specification are hereby incorporated by reference in their entireties.

BACKGROUND OF THE INVENTION

The immune response is a mechanism by which the body defends itself against foreign substances that invade it, causing infection or disease. This mechanism is based on the ability of antibodies produced or administered to the host to bind the antigen though its variable region. Once the antigen is bound by the antibody, the antigen is targeted for destruction, often mediated in part, by the constant region or Fc domain of the antibody.

For example, one activity of the Fc domain of the antibody is to bind complement proteins which can assist in lysing the target antigen, for example, a cellular pathogen. Another activity of the Fc region is to bind to Fc receptors (FcR) on the surface of immune cells, or so-called effector cells, which have the ability to trigger other immune effects. These immune effects include, for example, release of immune activators, regulation of antibody production, endocytosis, phagocytosis, and cell killing. In some clinical applications these responses are crucial for the efficacy of the antibody while in other cases they provoke unwanted side effects. One example of an effector-mediated side effect is the release of inflammatory cytokines causing an acute fever reaction. Another example is the long term deletion of antigen-bearing cells.

The effector function of an antibody can be avoided by using antibody fragments lacking the Fc region (e.g., such as a Fab, Fab'2, or single chain antibody (sFv)) however these fragments have a reduced half-life, only one antigen binding site instead of two (e.g., in the case of Fab antibody fragments and single chain antibodies (sFv)), and are more difficult to purify.

Currently there are limited ways to reduce the effector function of an antibody while retaining the other valuable attributes of the Fc region. One approach is to mutate amino acids on the surface of the antibody that are involved in the effector binding interactions. While some mutations lead to a reduction of effector function, residual activity usually remains. Moreover, these added mutations can make the antibody immunogenic.

Another approach to reduce effector function is to remove sugars that are linked to particular residues in the Fc region, by for example, deleting or altering the residue the sugar is attached to, removing the sugars enzymatically, by producing the antibody in cells cultured in the presence of a glycosylation inhibitor, or by expressing the antibody in cells unable to glycosylate proteins. However, the forgoing approaches leave residual effector function both in the form of complement-dependent cytolytic activity and Fc receptor binding. Thus, a further decrease in effector function would be important to guarantee complete ablation of activity.

Accordingly, a need exists for an improved method of making aglycosylated antibodies with altered or reduced effector function.

SUMMARY OF THE INVENTION

The invention solves the foregoing problems of glycosylated antibodies, indeed of any Fc-containing protein, by providing improved methods for producing aglycosylated antigen binding proteins, for example, aglycosylated antibodies, more specifically, aglycosylated IgG antibodies, by introducing only minimal alterations. In particular, the invention provides a method for introducing an amino acid alteration at a first amino acid residue position which results in the reduced glycosylation of the polypeptide at a different or second amino acid residue position. The first amino acid can be modified to comprise a desirable side chain chemistry such that it can be linked, for example, to an additional functional moiety, such as a blocking moiety, detectable moiety, diagnostic moiety, or therapeutic moiety. The resulting aglycosylated antigen binding polypeptides, for example, aglycosylated IgG antibody has, for example, altered or reduced effector function. The decrease in undesired effector function provided by the polypeptides and methods of the invention was surprisingly more substantial than other conventional means of aglycosylating Fc regions.

Accordingly, the invention has several advantages which include, but are not limited to, the following:

providing aglycosylated antigen binding polypeptides, for example, aglycosylated IgG antibodies, suitable as therapeutics because of their reduced effector function;

an efficient method of producing aglycosylated antibodies with minimal alterations to the polypeptide;

an efficient method of producing aglycosylated antibodies while also providing a site for linking a desirable functional moiety, such as a blocking moiety, detectable moiety, diagnostic moiety, or therapeutic moiety;

a method of altering the effector function of an antibody while avoiding any increase in immunogenicity; and methods for treating a subject in need of an aglycosylated antigen binding polypeptide therapy.

Accordingly, in one aspect, the invention provides a polypeptide, or variant polypeptide, containing an Fc region, wherein the Fc region has a modified first amino acid residue having a preferred side chain chemistry, and a second amino acid residue having reduced glycosylation as compared to an unmodified polypeptide or parent polypeptide.

In certain embodiments, the side chain chemistry of the first amino acid residue can be linked, for example, covalently linked, to an additional moiety, i.e., a functional moiety such as, for example, a blocking moiety, detectable moiety, diagnostic moiety, and/or therapeutic moiety.

In one embodiment, the functional moiety is a blocking moiety, in that the moiety inhibits or blocks glycosylation of the polypeptide at the second amino acid residue. The blocking moiety can also function to block effector function, for example, by inhibiting the binding of the Fc region of the polypeptide to an Fc receptor or complement protein.

In a preferred embodiment, the blocking moiety is a cysteine adduct which forms when the first amino acid residue is a cysteine or has a side chain chemistry comprising a thiol.

In certain embodiments, the first amino acid comprises a cysteine, cysteine adduct, cystine, mixed disulfide adduct, or disulfide linkage.

In another preferred embodiment, the blocking moiety is a polyalkylene glycol moiety, for example, a PEG moiety and preferably a PEG-maleimide moiety.

In a related embodiment, to the first amino acid of the polypeptide is a cysteine or has a side chain chemistry comprising a thiol and the PEG moiety is attached thereto.

In certain embodiments, the cysteine or thiol side chain chemistry is reduced to remove such cysteine adduct, cystine, mixed disulfide adduct, or disulfide linkage, and the PEG moiety is subsequently attached to the cysteine residue or thiol side chain.

In another embodiment, the functional moiety is a detectable moiety, such as, but not limited to, a fluorescent moiety or isotopic moiety.

In another embodiment, the functional moiety is a diagnostic moiety, which is a moiety capable of revealing the presence of a disease or disorder.

In another embodiment, the functional moiety is a therapeutic moiety such as, but not limited to, an anti-inflammatory agent, anti-cancer agent, anti-neurodegenerative agent, or anti-infective agent.

In another aspect, the variant polypeptide of a parent polypeptide comprises an Fc region with a modified first amino acid residue, wherein the modified first amino acid is spatially positioned such that reduced glycosylation at a second amino acid is achieved. In a preferred embodiment, the variant polypeptide, which is aglycosylated, also has reduced effector function, as compared to the parent polypeptide.

In a related embodiment, the modified first amino acid is spatially positioned from the second amino acid by an interval of at least 1 amino acid position or more, for example, by about 2, 3, 4, 5, 6, 7, 8, 9, or 10 amino acid residue positions or more.

In one embodiment, the modified first amino acid residue has a preferred side chain chemistry. In a related embodiment, the preferred side chain chemistry is of sufficient steric bulk and/or charge such that the polypeptide displays reduced glycosylation and/or effector function.

In one embodiment, the reduced effector function is reduced binding to an Fc receptor (FcR), such as FcγRI, FcγRII, FcγRIII, and/or FcγRIIIb.

In another embodiment, the reduced effector function is reduced binding to a complement protein, such as C1q.

In a related embodiment, the reduced binding is by a factor of about 1-fold to about 15-fold or more.

In another embodiment, the polypeptide has a first amino acid residue and second amino acid residue that are near or within a glycosylation motif, for example, an N-linked glycosylation motif that contains the amino acid sequence NXT or NXS. In a particular embodiment, the polypeptide of the method has a first amino acid residue modified by an amino acid substitution. In a related embodiment, the first amino acid residue is amino acid 299 and the second amino acid residue is amino acid 297, according to the Kabat numbering.

In another embodiment, the amino acid substitution is selected from the group consisting of T299A, T299N, T299G, T299Y, T299C, T299H, T299E, T299D, T299K, T299R, T299G, T299I, T299L, T299M, T299F, T299P, T299W, and T299V according to the Kabat numbering.

In a particular embodiment, the amino acid substitution is T299C or T299A.

In another embodiment, the polypeptide of the invention is pegylated at the modified first amino acid residue, for example, a cysteine residue, and in particular, with PEG-maleimide.

In a preferred embodiment, the polypeptide is an antibody, for example, an antibody having an Fc region obtained from an antibody such as IgG1, IgG2, IgG3, or IgG4, and preferably, IgG1 or IgG4.

In yet another embodiment, the foregoing polypeptide displays altered effector function, for example, reduced binding to an Fc receptor (FcR) (such as FcγRI, FcγRII, or FcγRIII) or reduced binding to a complement protein, such as C1q.

In another embodiment, the forgoing polypeptide binds to an antigen such as a ligand, cytokine, receptor, cell surface antigen, or cancer cell antigen.

In another embodiment, the foregoing polypeptide is in a suitable pharmaceutical carrier.

In a another aspect, the invention provides an isolated nucleic acid encoding any one of the foregoing polypeptides, wherein the nucleic acid can be encoded in a vector, such that, for example, the nucleic acid or vector encoding the same can be expressed in a host cell.

In a another aspect, the invention provides a method for producing an antigen binding polypeptide by culturing the foregoing host cell containing a nucleic acid encoding a polypeptide of the invention under suitable culture conditions for producing the polypeptide followed by, for example, recovering the polypeptide from the host cell culture.

In a another aspect, the invention provides a method of producing a modified antigen binding polypeptide having reduced glycosylation in an Fc region, by identifying an original first amino acid residue in an original polypeptide and a second amino acid residue capable of being glycosylated in an Fc region of the original polypeptide, and modifying the original first amino acid residue in the original polypeptide to produce a modified first amino acid in a modified polypeptide, such that glycosylation of the second amino acid residue of the Fc region is decreased in the modified or variant polypeptide as compared to the original or parent polypeptide.

In one embodiment, the method can comprise the step of determining if the modified antigen binding polypeptide displays altered effector function.

In another aspect, the invention provides a method of reducing effector function by identifying a first amino acid residue in the antibody, which when modified, is capable of altering the glycosylation of the second amino acid residue in the Fc region of the antibody. The identifying of the first amino acid residue to be modified can be computer-assisted using, for example, art recognized modeling software. The first amino acid residue is then modified such that glycosylation of the second amino acid residue of the Fc region is reduced in the modified antibody as compared to the unmodified parent antibody.

In another aspect, the invention provides a polypeptide produced by any one of the foregoing methods.

In another aspect, the invention provides a method of diagnosing, treating, or preventing a disease or disorder in an animal, for example, a human patient, by administering a polypeptide of the invention having reduced glycosylation and/or effector function.

Other features and advantages of the invention will be apparent from the following detailed description and claims.

DETAILED DESCRIPTION OF THE INVENTION

Figure 1:
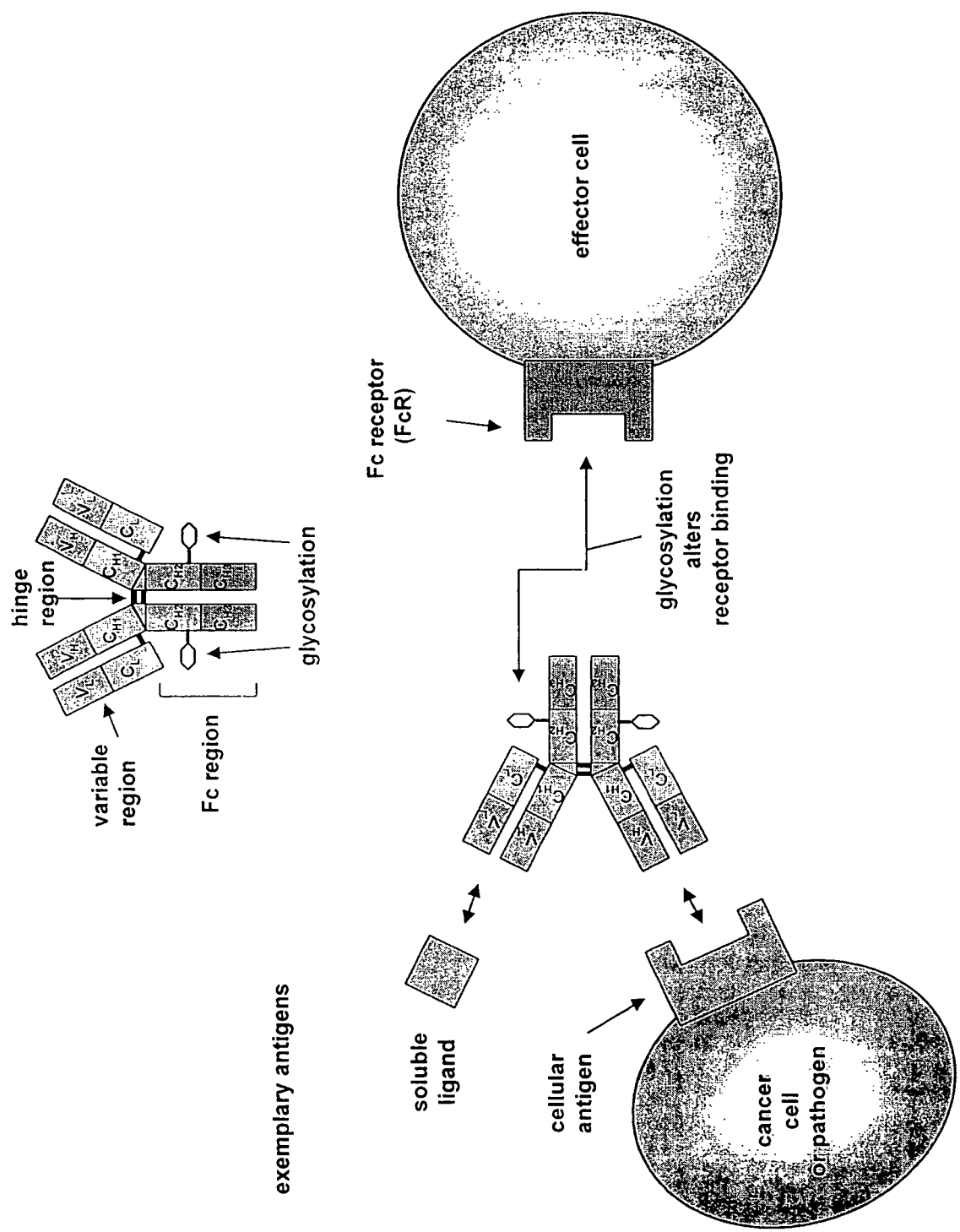
FIG. 1 depicts the structure of a typical antigen binding polypeptide (IgG antibody) and the functional properties of antigen binding and effector function (e.g., Fc receptor (FcR) binding) of an antibody. Also shown is how the presence of sugars (glycosylation) in the CH2 domain of the antibody alters effector function (FcR binding) but does not affect antigen binding.
Figure 2:
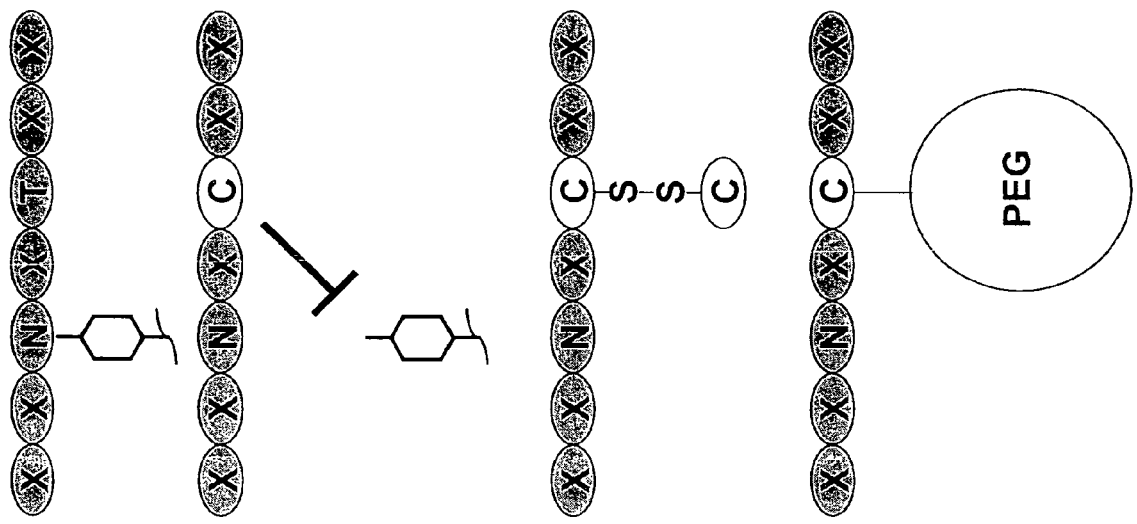
FIG. 2 depicts the structure and sequence of an Fc region of an antibody of the invention where a residue proximal to the glycosylated amino acid reside can be altered to inhibit glycosylation (left panel). Also shown (right panel) is that if the first amino acid reside is a cysteine, glycosylation is not only inhibited but the cysteine residue provides a site for linking a functional moiety, e.g., a blocking moiety, such as a cysteine adduct or pegylation moiety (shown) or other functional moieties (not shown).
Figure 2:
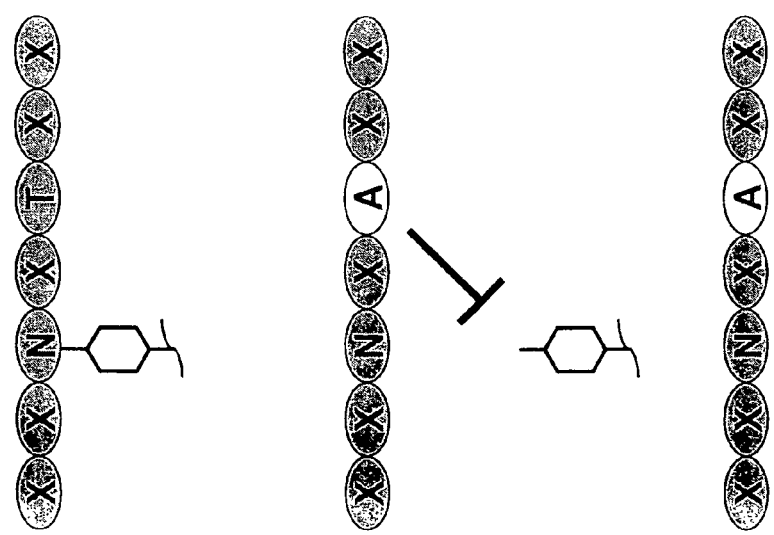

In order to provide a clear understanding of the specification and claims, the following definitions are conveniently provided below.

DEFINITIONS

The term "antibody" includes monoclonal antibodies (including full length monoclonal antibodies), polyclonal antibodies, multispecific antibodies (e.g., bispecific antibodies), chimeric antibodies, CDR-grafted antibodies, humanized antibodies, human antibodies, and fragments thereof where reduced glycosylation and/or effector function is desirable, for example, an antibody light chain (VL), an antibody heavy chain (VH), a single chain antibody (scFv), a F(ab')2 fragment, a Fab fragment, an Fd fragment, an Fv fragment, and a single domain antibody fragment (DAb).

The term "parent antibody" includes any antibody for which modification of the glycosylation, effector function, and/or the providing of a preferred or desirable side chain chemistry for adding, for example, a functional moiety, is desired. Thus, the parent antibody represents the original antibody on which the methods of the instant invention are performed. The parent polypeptide may comprise a native sequence (i.e. a naturally occurring) antibody (including a naturally occurring allelic variant), or an antibody with pre-existing amino acid sequence modifications (such as insertions, deletions and/or other alterations) of a naturally occurring sequence. The parent antibody may be a monoclonal, chimeric, CDR-grafted, humanized, or human antibody.

The terms "antibody variant" or "modified antibody", includes an antibody which has an amino acid sequence or amino acid side chain chemistry which differs from that of the parent antibody by at least one amino acid or amino acid modification as described herein. In preferred embodiments, the antibody variant will have reduced glycosylation, and, optionally, reduced effector function as compared to the parent antibody and/or further comprise one or more functional moieties.

The term "first amino acid residue" refers to the amino acid residue (or position) of the polypeptide which is modified by the insertion, substitution, or deletion of an amino acid residue or by directly altering the side chain chemistry of the existing amino acid residue, such that the modified amino acid residue (or residue position) is different and thereby reduces or eliminates glycosylation of a second amino acid residue. Preferably, the modification of the first amino acid, while influencing the glycosylation and/or effector function of the polypeptide (and optionally providing a site for linking a functional moiety), the modification does not significantly alter other desired functions of the polypeptide nor does the functional moiety attached thereto. For example, where the Fc containing polypeptide is an antibody, the modification of the first amino acid does not significantly alter the antigen-binding activity of the antibody.

The term "second amino acid residue" refers to the amino acid residue of the polypeptide which is capable of being covalently linked to one or more carbohydrates, for example, glycosylated.

The term "preferred side chain chemistry" refers to a chemistry, for example, an amino acid residue side chain or R-group chemistry that imparts a desirable characteristic to the polypeptide. The preferred side chain chemistry is introduced at the first amino acid position by amino acid substitution, by chemical substitution such that its side chain chemistry is modified, or by an amino acid addition or deletion such that a different amino acid side chain chemistry is provided at the first amino acid position. As described herein, modification of the side chain chemistry of the parent antibody so that it contains the preferred side chain chemistry reduces glycosylation at a second amino acid position, resulting in reduced effector function. The modification also provides a site for linking a desirable functional moiety. In certain embodiments, a determination as to the preferred side chain chemistry may be informed by an in silico or computer-based approach for determining the steric bulk, and/or charge of the side chain chemistry to be introduced (e.g., by substitution) at the first amino acid position.

The term "amino acid" includes alanine (Ala or A); arginine (Arg or R); asparagine (Asn or N); aspartic acid (Asp or D); cysteine (Cys or C); glutamine (Gln or Q); glutamic acid (Glu or E); glycine (Gly or G); histidine (His or H); isoleucine (Ile or I): leucine (Leu or L); lysine (Lys or K); methionine (Met or M); phenylalanine (Phe or F); proline (Pro or P); serine (Ser or S); threonine (Thr or T); tryptophan (Trp or W); tyrosine (Tyr or Y); and valine (Val or V). Non-traditional amino acids are also within the scope of the invention and include norleucine, ornithine, norvaline, homoserine, and other amino acid residue analogues such as those described in Ellman et al. Meth. Enzym. 202:301-336 (1991). To generate such non-naturally occurring amino acid residues, the procedures of Noren et al. Science 244:182 (1989) and Ellman et al., supra, can be used. Briefly, these procedures involve chemically activating a suppressor tRNA with a non-naturally occurring amino acid residue followed by in vitro transcription and translation of the RNA. Introduction of the non-traditional amino acid can also be achieved using peptide chemistries know in the art.

The term "preferred side chain chemistry is of sufficient steric bulk" includes the side chain chemistry of an amino acid residue having sufficient steric bulk so as to inhibit the glycosylation of an Fc containing polypeptide and/or its effector function. Such residues include, for example, phenylalanine, tyrosine, tryptophan, arginine, lysine, histidine, glutamic acid, glutamine, and methionine, or analogs or mimetics thereof.

The term "preferred side chain chemistry is of sufficient charge" or "electrostatic charge" includes the side chain chemistry of an amino acid residue having sufficient charge so as to inhibit the glycosylation of an Fc containing polypeptide and/or its effector function. Such residues include, for example, the negatively charged amino acid residues, e.g., aspartic acid, glutamic acid, or analogs or mimetics thereof, and the positively charged amino acid residues, e.g., lysine, arginine, histidine, and analogs or mimetics thereof.

The term "preferred side chain chemistry is of sufficient steric bulk and charge" includes the side chain chemistry of an amino acid residue having sufficient steric bulk and charge so as to inhibit the glycosylation of an Fc containing polypeptide and/or its effector function. Such residues include, for example, lysine, arginine, tyrosine, and analogs or mimetics thereof.

The term "sufficient" as used herein, generally refers to the preferred modifications described herein which achieve at least one of the following in an Fc containing polypeptide: reduced glycosylation of the polypeptide; reduced effector function of the polypeptide; and/or providing of a site for linking a functional moiety.

The term "functional moiety" includes moieties which, preferably, add a desirable function to the variant polypeptide. Preferably, the function is added without significantly altering an intrinsic desirable activity of the polypeptide, e.g., in the case of an antibody, the antigen-binding activity of the molecule. A variant polypeptide of the invention may comprise one or more functional moieties, which may be the same or different. Examples of useful functional moieties include, but are not limited to, a blocking moiety, a detectable moiety, a diagnostic moiety, and a therapeutic moiety. Exemplary blocking moieties include moieties of sufficient steric bulk and/or charge such that reduced glycosylation occurs, for example, by blocking the ability of a glycosidase to glycosylate the polypeptide. The blocking moiety may additionally or alternatively, reduce effector function, for example, by inhibiting the ability of the Fc region to bind a receptor or complement protein. Preferred blocking moieties include cysteine adducts, cystine, mixed disulfide adducts, and PEG moieties. Exemplary detectable moieties include fluorescent moieties, radioisotopic moieties, radiopaque moieties, and the like. Exemplary diagnostic moieties include moieties suitable for revealing the presence of an indicator of a disease or disorder. Exemplary therapeutic moieties include, for example, anti-inflammatory agents, anti-cancer agents, anti-neurodegenerative agents, and anti-infective agents. The functional moiety may also have one or more of the above-mentioned functions. Other useful functional moieties are known in the art and described, below.

The term "pegylation", "polyethylene glycol", or "PEG" includes a polyalkylene glycol compound or a derivative thereof, with or without coupling agents or derviatization with coupling or activating moieties (e.g., with thiol, triflate, tresylate, azirdine, oxirane, or preferably with a maleimide moiety, e.g., PEG-maleimide). Other appropriate polyalkylene glycol compounds include, but are not limited to, maleimido monomethoxy PEG, activated PEG polypropylene glycol, but also charged or neutral polymers of the following types: dextran, colominic acids, or other carbohydrate based polymers, polymers of amino acids, and biotin derivatives.

The term "spatially positioned" includes the relative position or distance between the modified first amino acid position and the second amino acid position within a polypeptide where it is desirable to alter or reduce the glycosylation at the second amino acid position by modifying the first amino acid position. Amino acid distances of about 1, 2, 3, 4, 5, 6, 7, 8, 9, 10, 10-20 or more amino acid positions, or any interval of the foregoing ranges are within the scope of the invention. Methods of determining that the desired spatial positioning of the first and second amino acids achieves the desired effect, for example, reduced glycosylation and/or effector function, are known in the art and are described herein (see, e.g., Examples 1 and 4).

The term "effector function" refers to the functional ability of the Fc or constant region of an antibody to bind proteins and/or cells of the immune system. Typical effector functions include the ability to bind complement protein (e.g., the complement protein C1q), and/or an Fc receptor (FcR) (e.g., FcγRI, FcγRII, FcγRIII, and/or FcγRIIIb). The functional consequences of being able to bind one or more of the foregoing include opsonization, phagocytosis, antigen-dependent cellular cytotoxicity (ADCC), complement-dependent cytotoxicity (CDC) and/or effector cell modulation. A decrease in effector function refers to a decrease in one or more of the biochemical or cellular activities, while maintaining the antigen binding activity of the variable region of the antibody (or fragment thereof). Decreases in effector function, e.g., Fc binding to an Fc receptor or complement protein, can be expressed in terms of fold reduction (e.g., reduced by 1-fold, 2-fold, and the like) and can be calculated based on, e.g., the percent reductions in binding activity determined using the assays described herein (see, e.g., Example 4) or assays known in the art.

The term "glycosylation" refers to the covalent linking of one or more carbohydrates to a polypeptide. Typically, glycosylation is a posttranslational event which can occur within the intracellular milieu of a cell or extract therefrom. The term glycosylation includes, for example, N-linked glycosylation (where one or more sugars are linked to an asparagine residue) and/or O-linked glycosylation (where one or more sugars are linked to an amino acid residue having a hydroxyl group (e.g., serine or threonine).

All amino acid numberings herein for an Fc region of a polypeptide correspond to the Kabat numbering system as described, e.g., by Kabat et al., in "Sequences of Proteins of Immunological Interest", U.S. Dept. Health and Human Services, 1983 and 1987.

DETAILED DESCRIPTION

A method has been developed to produce aglycosylated antigen-binding polypeptides, for example, antibodies or Fc-containing fusion proteins, by altering a first amino acid residue that inhibits the glycosylation at a second amino acid residue. The method is especially well suited for producing therapeutic aglycosylated Fc-containing polypeptides in eukaryotic cells with only minimal amino acid alterations to the polypeptide. The methods of the present invention thereby avoids introducing into the polypeptide amino acid sequence that can be immunogenic.

Preferably, the modification of the first amino acid, while influencing the glycosylation and/or effector function of the polypeptide (and optionally providing a site for linking a functional moiety), does not significantly alter other desired functions of the polypeptide nor does the functional moiety attached thereto. For example, where the Fc containing polypeptide is an antibody, the modification of the first amino acid does not significantly alter the antigen-binding activity of the antibody.

Accordingly, the method is suitable for producing therapeutic antibodies, for example, IgG antibodies, where altered or reduced effector function is desired. The altered or reduced effector function is achieved by reducing or eliminating the glycosylation of the Fc region of the antibody using the method of the invention (FIG. 1). In particular, a first amino acid residue(s) is targeted for alteration (e.g., by substitution, insertion, deletion, or by chemical modification) which inhibits the glycosylation of a second amino acid residue. The resultant antibody is aglycosylated at the second amino acid residue and has altered or reduced effector function, e.g., complement binding activity or effector cell activity such as binding to an Fc receptor.

In certain embodiments, the reduced effector function is reduced binding to an Fc receptor (FcR), such as the FcγRI, FcγRII, FcγRIII, and/or FcγRIIIb receptor or a complement protein, for example, the complement protein C1q. This change in binding can be by a factor of about 1 fold or more, e.g., by about 2, 3, 4, 5, 6, 7, 8, 9, 10, 15, 50, or 100-fold or more, or by any interval or range thereof.

These decreases in effector function, e.g., Fc binding to an Fc receptor or complement protein, are readily calculated based on, e.g., the percent reductions in binding activity determined using the assays described herein (see, e.g., Example 4) or assays known in the art.

In another embodiment, the first amino acid residue is modified or substituted to contain a preferred side chain chemistry of sufficient steric bulk and/or charge such that reduced glycosylation and or effector function is achieved.

Exemplary amino acid residues having side chain chemistry of sufficient steric bulk include phenylalanine, tyrosine, tryptophan, arginine, lysine, histidine, glutamic acid, glutamine, and methionine, or analogs or mimetics thereof.

Exemplary amino acid residues having side chain chemistry of sufficient charge include, for example, negatively charged amino residues, e.g., aspartic acid, glutamic acid analogs or mimetics thereof, and positively charged amino acid residues, e.g., lysine, arginine, histidine, and analogs or mimetics thereof.

Further, amino acid residues that are uncharged at physiological pH may become charged when residing in an environment that alters the physiological pH, e.g., serine, threonine, cysteine, methionine, asparagine, glutamine, tyrosine, and analogs or mimetics thereof. For example, uncharged amino acid residues can be buried inside a folded protein and experience a shift in pKa, thereby altering the charge of the residue compared to the charge at physiological pH.

In one embodiment, the preferred amino acid residue is of sufficient steric bulk and charge such that the residue inhibits glycosylation at a second amino acid position. Such amino acids include, for example, lysine, arginine, and tyrosine.

In preferred embodiments of the present invention, the amino acid residue that is modified can be selected for additional properties, e.g., to serve as a site for coupling desirable functional moieties which impart desirable properties to the polypeptide. Examples of such preferred moieties include, e.g., blocking moieties, detectable moieties, diagnostic moieties, and therapeutic moieties.

In another embodiment, the variant polypeptide of a parent polypeptide contains an Fc region, which comprises a modified first amino acid residue, wherein the modified first amino acid is spatially positioned such that reduced glycosylation at a second amino acid is achieved, whereby the variant polypeptide has reduced effector function as compared to the parent polypeptide.

Preferred spatial positioning can be based on the predicted proximity of the first amino acid to the second amino acid as well as the steric bulk and/or charge of the preferred side chain chemistry to be introduced at the first amino acid position. Alternatively, a determination as to the optimal spatial positioning may be informed by empirical observations after substitutions of a preferred amino acid side chain chemistry at one or more positions and/or using an art recognized in silico or computer-based approach for determining the steric bulk, charge, and/or the distance of the first amino acid position from the second amino acid position. Amino acid distances of about 1, 2, 3, 4, 5, 6, 7, 8, 9, 10, 10-20 or more residue positions, or any interval of the foregoing ranges, are within the scope of the invention. Thus, in certain preferred embodiments, the modified first amino acid is spatially positioned from the second amino acid by an interval of at least 1 amino acid position or more, for example, by 2, 3, 4, 5, 6, 7, 8, 9, or 10 amino acid positions or more.

Methods of determining that the desired spatial positioning of the first and second amino acids achieves the desired effect, for example, reduced glycosylation and/or effector function, are described herein (see, e.g., Examples 1 and 4).

In a preferred embodiment, the polypeptide of the invention is an Fc containing polypeptide such as an antibody, and preferably IgG immunoglobulin, e.g., of the subtype IgG1, IgG2, IgG3, or IgG4, and preferably, of the subtype IgG1 or IgG4. In a preferred embodiment, the forgoing polypeptide binds to an antigen such as a ligand, cytokine, receptor, cell surface antigen, or cancer cell antigen.

Because the invention provides an isolated nucleic acid encoding any one of the foregoing polypeptides, the nucleic acid can be introduced into a vector and expressed in a host cell. Accordingly, a polypeptide of the invention can be produced by culturing a suitable host cell containing a nucleic acid encoding a polypeptide of the invention under appropriate culture conditions for producing the polypeptide.

In a preferred embodiment, the polypeptide of the invention has a first amino acid that has been modified to have a cysteine residue or side chain chemistry thereof, i.e., a thiol, such that the polypeptide, under the above culture conditions, is capable of forming an adduct with a free cysteine provided under the culture conditions. In a preferred embodiment, the resulting polypeptide has reduced glycosylation and effector function.

In a related embodiment, the polypeptide can be further manipulated, for example, subjected to reducing conditions, such that the cysteine adduct, cystine, mixed disulfide adduct, or disulfide linkage, is removed thereby providing a site for further modifying the polypeptide with a functional moiety, for example, a pegylation moiety.

In another embodiment, the polypeptide has a first amino acid residue and second amino acid residue that are near or within a glycosylation motif, for example, an N-linked glycosylation motif that contains the amino acid sequence NXT or NXS. In a particular embodiment, the polypeptide of the method has a first amino acid residue modified by an amino acid substitution. In a related embodiment, the first amino acid residue is amino acid 299 and the second amino acid residue is amino acid 297, according to the Kabat numbering.

In another embodiment, the amino acid substitution is selected from the group consisting of T299A, T299N, T299G, T299Y, T299C, T299H, T299E, T299D, T299K, T299R, T299G, T2991, T299L, T299M, T299F, T299P, T299W, and T299V according to the Kabat numbering.

In a particular embodiment, the amino acid substitution is T299C or T299A.

Although the method of the invention described herein uses an IgG antibody that is normally N-glycosylated at a particular residue in the Fc region (amino acid 297) (FIGS. 1-2), it is understood that the method can be equally applied to an Fc region within any polypeptide. When the polypeptide is an antibody, the antibody can be synthetic, naturally-derived (e.g., from serum), produced by a cell line (e.g., a hybridoma), or produced in a transgenic organism. Still further, the method may also be applied to a polypeptide which does not comprise an Fc region provided the polypeptide comprises at least one glycosylation site.

The method offers several advantages over current mutagenesis methods, for example, because the method can be used to inhibit glycosylation of the polypeptide in a way that is minimally disruptive (FIG. 2, left panel), e.g., without the mutation of the normally glycosylated residue, deletion of the glycosylation site, or enzymatic removal of the sugar moieties. Accordingly, the structure of the polypeptide is maintained, the binding affinity of the polypeptide for antigen is maintained, immunogenicity of the polypeptide is avoided, and the polypeptide can be, if desired, coupled to a desirable functional moiety (FIG. 2, right panel). Such functional moieties can further abrogate effector function or improve the half-life of the polypeptide or achieve desirable therapeutic function. Moreover, the methods of the invention can be performed using standard genetic engineering techniques.

1. Identifying Glycosylation Sites

The method is performed by identifying a glycosylation site in an Fc-containing polypeptide, for example, an antibody, in one embodiment, an IgG antibody. The identification of the glycosylation site can be experimental or based on sequence analysis or modeling data. Consensus motifs, that is, the amino acid sequence recognized by various glycosyl transferases, have been described. For example, the consensus motif for an N-linked glycosylation motif is frequently NXT or NXS, where X can be any amino acid except proline (FIG. 2). Several algorithms for locating a potential glycosylation motif have also been described. Accordingly, to identify potential glycosylation sites within an antibody or Fc-containing fragment, the sequence of the antibody is examined, for example, by using publicly available databases such as the website provided by the Center for Biological Sequence Analysis (see the NetNGlyc 1.0 Server for predicting N-linked glycosylation sites) and the NetOGlyc 3.1 Server for predicting O-linked glycosylation sites). Additional methods for altering glycosylation sites of antibodies are described, e.g., in U.S. Pat. Nos. 6,350,861 and 5,714,350.

In certain cases, the glycosylation of a given motif will depend on other features of the protein, the type of cell or cell extract and the conditions under which the antibody is produced or contacted with such a cell or extract. To the extent that a given cell or extract has resulted in the glycosylation of a given motif, art recognized techniques for determining if the motif has been glycosylated are available, for example, using gel electrophoresis and/or mass spectroscopy, as described herein.

Identification of an actual or potential glycosylation motif also reveals the residue to which the sugars are covalently linked. For example, N-linked glycosylation results in the linking of a sugar residue (glycan) to the terminal side-chain nitrogen at an asparagine residue. In another example, O-linked glycosylation results in the covalent linking of a sugar residue (glycan) to an amino acid reside having a hydroxyl side group such as serine or threonine. In either case, the method of the invention does not alter the residue to which one or more sugars would be covalently linked. Rather, the method of the invention employs the alteration of a residue different from the residue which would be normally covalently linked to a sugar residue by a mechanism that operates in cis thereby inhibiting the coupling of one or more sugars to the residue but without requiring the alteration of the actual residue capable of being linked to a sugar, i.e., glycosylated.

The methods of the invention are applicable to a variety of uses including, the bioproduction of aglycosylated polypeptides using eukaryotic cells. Such aglycosylated polypeptides, for example, antibodies, are desirable therapeutics for the treatment of human disease.

2. Production of Antibodies with Altered Fc Regions

Having selected the antibody to be improved, for example, a chimeric, human, humanized, or synthetic antibody, a variety of methods are available for producing such antibodies. Because of the degeneracy of the code, a variety of nucleic acid sequences will encode each antibody amino acid sequence. The desired nucleic acid sequences can be produced by de novo solid-phase DNA synthesis or by PCR mutagenesis of an earlier prepared polynucleotide encoding the antibody. Oligonucleotide-mediated mutagenesis is one method for preparing a substitution, deletion, or insertion of an alteration (e.g., altered codon) that reduces the glycosylation of a second, usually proximal, amino acid. For example, the target polypeptide DNA is altered by hybridizing an oligonucleotide encoding the desired mutation to a single-stranded DNA template. After hybridization, a DNA polymerase is used to synthesize an entire second complementary strand of the template that incorporates the oligonucleotide primer, and encodes the selected alteration in the variant polypeptide-DNA. In one embodiment, genetic engineering, e.g., primer-based PCR mutagenesis, is sufficient to alter the first amino acid, as defined herein, for producing a polynucleotide encoding a polypeptide that, when expressed in a eukaryotic cell, will now have an aglycosylated region, for example, aglycosylated Fc region. The antibodies produced as described above typically comprise at least a portion of an antibody constant region (Fc), typically that of a human immunoglobulin. Ordinarily, the antibody will contain both light chain and heavy chain constant regions. The heavy chain constant region usually includes CH1, hinge, CH2, and CH3 regions. It is understood, however, that the antibodies described herein include antibodies having all types of constant regions, including IgM, IgG, IgD, and IgE, and any isotype, including IgG1, IgG2, IgG3, and IgG4. In one embodiment, the human isotype IgG1 is used. In another embodiment, the human isotype IgG4 is used. Light chain constant regions can be lambda or kappa. The humanized antibody may comprise sequences from more than one class or isotype. Antibodies can be expressed as tetramers containing two light and two heavy chains, as separate heavy chains, light chains, as Fab, Fab' F(ab')2, and Fv, or as single chain antibodies (sFv) in which heavy and light chain variable domains are linked through a spacer.

Methods for determining the effector function of a polypeptide comprising an Fc region, for example, an antibody, are described herein and include cell-based bridging assays to determine changes in the ability of a modified Fc region to bind to an Fc receptor. Other binding assays may be used to determine the ability of an Fc region to bind to a complement protein, for example, the C1q complement protein. Additional techniques for determining the effector function of a modified Fc region are described in the art.

3. Functional Moieties and the Chemistry of Linking Such Moieties to Fc-Containing Polypeptides The invention provides antibodies and Fc-containing polypeptides that may be further modified to provide a desired effect. For example, in preferred embodiments, the first amino acid is modified to be a residue that not only alters the glycosylation of the polypeptide at a second site, but also provides a desired side chain chemistry.

In certain preferred embodiments, the side chain chemistry of the amino acid residue is capable of being linked, for example, covalently linked, to an additional moiety, i.e., a functional moiety such as, for example, a blocking moiety, a detectable moiety, a diagnostic moiety, and/or a therapeutic moiety. Exemplary functional moieties are first described below followed by useful chemistries for linking such functional moieties to the different amino acid side chain chemistries.

3.1 Functional Moieties

Examples of useful functional moieties include, but are not limited to, a blocking moiety, a detectable moiety, a diagnostic moiety, and a therapeutic moiety.

Exemplary blocking moieties include moieties of sufficient steric bulk and/or charge such that reduced glycosylation occurs, for example, by blocking the ability of a glycosidase to glycosylate the polypeptide. The blocking moiety may additionally or alternatively, reduce effector function, for example, by inhibiting the ability of the Fc region to bind a receptor or complement protein. Preferred blocking moieties include cysteine adducts and PEG moieties.

In a preferred embodiment, the blocking moiety is a cysteine, preferably a cysteine that has associated with a free cysteine, e.g., during or subsequent to the translation of the Fc containing polypeptide, e.g., in cell culture. Other blocking cysteine adducts include cystine, mixed disulfide adducts, or disulfide linkages.

In another preferred embodiment, the blocking moiety is a polyalkylene glycol moiety, for example, a PEG moiety and preferably a PEG-maleimide moiety. Preferred pegylation moieties (or related polymers) can be, for example, polyethylene glycol ("PEG"), polypropylene glycol ("PPG"), polyoxyethylated glycerol ("POG") and other polyoxyethylated polyols, polyvinyl alcohol ("PVA") and other polyalkylene oxides, polyoxyethylated sorbitol, or polyoxyethylated glucose. The polymer can be a homopolymer, a random or block copolymer, a terpolymer based on the monomers listed above, straight chain or branched, substituted or unsubstituted as long as it has at least one active sulfone moiety. The polymeric portion can be of any length or molecular weight but these characteristics can affect the biological properties. Polymer average molecular weights particularly useful for decreasing clearance rates in pharmaceutical applications are in the range of 2,000 to 35,000 daltons. In addition, if two groups are linked to the polymer, one at each end, the length of the polymer can impact upon the effective distance, and other spatial relationships, between the two groups. Thus, one skilled in the art can vary the length of the polymer to optimize or confer the desired biological activity. PEG is useful in biological applications for several reasons. PEG typically is clear, colorless, odorless, soluble in water, stable to heat, inert to many chemical agents, does not hydrolyze, and is nontoxic. Pegylation can improve pharmacokinetic performance of a molecule by increasing the molecule's apparent molecular weight. The increased apparent molecular weight reduces the rate of clearance from the body following subcutaneous or systemic administration. In many cases, pegylation can decrease antigenicity and immunogenicity. In addition, pegylation can increase the solubility of a biologically-active molecule.

Pegylated antibodies and antibody fragments may generally be used to treat conditions that may be alleviated or modulated by administration of the antibodies and antibody fragments described herein. Generally the pegylated aglycosylated antibodies and antibody fragments have increased half-life, as compared to the nonpegylated aglycosylated antibodies and antibody fragments. The pegylated aglycosylated antibodies and antibody fragments may be employed alone, together, or in combination with other pharmaceutical compositions.

Examples of detectable moieties which are useful in the methods and polypeptides of the invention include fluorescent moieties, radioisotopic moieties, radiopaque moieties, and the like, e.g. detectable labels such as biotin, fluorophores, chromophores, spin resonance probes, or radiolabels. Exemplary fluorophores include fluorescent dyes (e.g. fluorescein, rhodamine, and the like) and other luminescent molecules (e.g. luminal). A fluorophore may be environmentally-sensitive such that its fluorescence changes if it is located close to one or more residues in the modified protein that undergo structural changes upon binding a substrate (e.g. dansyl probes). Exemplary radiolabels include small molecules containing atoms with one or more low sensitivity nuclei ($^{13}C$, $^{15}N$, $^{2}H$, $^{125}I$, $^{123}I$, $^{99}Tc$, $^{43}K$, $^{52}Fe$, $^{67}Ga$, $^{68}Ga$, $^{111}In$ and the like). Other useful moieties are known in the art.

Examples of diagnostic moieties which are useful in the methods and polypeptides of the invention include detectable moieties suitable for revealing the presence of a disease or disorder. Typically a diagnostic moiety allows for determining the presence, absence, or level of a molecule, for example, a target peptide, protein, or proteins, that is associated with a disease or disorder. Such diagnostics are also suitable for prognosing and/or diagnosing a disease or disorder and its progression.

Examples of therapeutic moieties which are useful in the methods and polypeptides of the invention include, for example, anti-inflammatory agents, anti-cancer agents, anti-neurodegenerative agents, and anti-infective agents. The functional moiety may also have one or more of the above-mentioned functions.

Exemplary therapeutics include radionuclides with high-energy ionizing radiation that are capable of causing multiple strand breaks in nuclear DNA, and therefore suitable for inducing cell death (e.g., of a cancer). Exemplary high-energy radionuclides include: $^{90}Y$, $^{125}I$, $^{131}I$, $^{123}I$, $^{111}In$, $^{105}Rh$, $^{153}Sm$, $^{67}Cu$, $^{67}Ga$, $^{166}Ho$, $^{177}Lu$, $^{186}Re$ and $^{188}Re$. These isotopes typically produce high energy α- or β-particles which have a short path length. Such radionuclides kill cells to which they are in close proximity, for example neoplastic cells to which the conjugate has attached or has entered. They have little or no effect on non-localized cells and are essentially non-immunogenic.

Exemplary therapeutics also include cytotoxic agents such as cytostatics (e.g. alkylating agents, DNA synthesis inhibitors, DNA-intercalators or cross-linkers, or DNA-RNA transcription regulators), enzyme inhibitors, gene regulators, cytotoxic nucleosides, tubulin binding agents, hormones and hormone antagonists, anti-angiogenesis agents, and the like.

Exemplary therapeutics also include alkylating agents such as the anthracycline family of drugs (e.g. adriamycin, carminomycin, cyclosporin-A, chloroquine, methopterin, mithramycin, porfiromycin, streptonigrin, porfiromycin, anthracenediones, and aziridines). In another embodiment, the chemotherapeutic moiety is a cytostatic agent such as a DNA synthesis inhibitor. Examples of DNA synthesis inhibitors include, but are not limited to, methotrexate and dichloromethotrexate, 3-amino-1,2,4-benzotriazine 1,4-dioxide, aminopterin, cytosine β-D-arabinofuranoside, 5-fluoro-5'-deoxyuridine, 5-fluorouracil, ganciclovir, hydroxyurea, actinomycin-D, and mitomycin C. Exemplary DNA-intercalators or cross-linkers include, but are not limited to, bleomycin, carboplatin, carmustine, chlorambucil, cyclophosphamide, cis-diammineplatinum(II) dichloride (cisplatin), melphalan, mitoxantrone, and oxaliplatin.

Exemplary therapeutics also include transcription regulators such as actinomycin D, daunorubicin, doxorubicin, homoharringtonine, and idarubicin. Other exemplary cytostatic agents that are compatible with the present invention include ansamycin benzoquinones, quinonoid derivatives (e.g. quinolones, genistein, bactacyclin), busulfan, ifosfamide, mechlorethamine, triaziquone, diaziquone, carbazilquinone, indoloquinone EO9, diaziridinyl-benzoquinone methyl DZQ, triethylenephosphoramide, and nitrosourea compounds (e.g. carmustine, lomustine, semustine).

Exemplary therapeutics also include cytotoxic nucleosides such as, for example, adenosine arabinoside, cytarabine, cytosine arabinoside, 5-fluorouracil, fludarabine, floxuridine, ftorafur, and 6-mercaptopurine; tubulin binding agents such as taxoids (e.g. paclitaxel, docetaxel, taxane), nocodazole, rhizoxin, dolastatins (e.g. Dolastatin-10, -11, or -15), colchicine and colchicinoids (e.g. ZD6126), combretastatins (e.g. Combretastatin A-4, AVE-6032), and vinca alkaloids (e.g. vinblastine, vincristine, vindesine, and vinorelbine (navelbine)); anti-angiogenesis compounds such as Angiostatin K1-3, DL-α-difluoromethyl-ornithine, endostatin, fumagillin, genistein, minocycline, staurosporine, and (±)-thalidomide.

Exemplary therapeutics also include hormones and hormone antagonists, such as corticosteroids (e.g. prednisone), progestins (e.g. hydroxyprogesterone or medroprogesterone), estrogens, (e.g. diethylstilbestrol), antiestrogens (e.g. tamoxifen), androgens (e.g. testosterone), aromatase inhibitors (e.g. aminogluthetimide), 17-(allylamino)-17-demethoxygeldanamycin, 4-amino-1,8-naphthalimide, apigenin, brefeldin A, cimetidine, dichloromethylene-diphosphonic acid, leuprolide (leuprorelin), luteinizing hormone-releasing hormone, pifithrin-α, rapamycin, sex hormone-binding globulin, and thapsigargin.

Exemplary therapeutics also include enzyme inhibitors such as, S(+)-camptothecin, curcumin, (−)-deguelin, 5,6-dichlorobenz-imidazole 1-β-D-ribofuranoside, etoposide, formestane, fostriecin, hispidin, 2-imino-1-imidazo-lidineacetic acid (cyclocreatine), mevinolin, trichostatin A, tyrphostin AG 34, and tyrphostin AG 879.

Exemplary therapeutics also include gene regulators such as 5-aza-2'-deoxycytidine, 5-azacytidine, cholecalciferol (vitamin $D_3$), 4-hydroxytamoxifen, melatonin, mifepristone, raloxifene, trans-retinal (vitamin A aldehydes), retinoic acid, vitamin A acid, 9-cis-retinoic acid, 13-cis-retinoic acid, retinol (vitamin A), tamoxifen, and troglitazone.

Exemplary therapeutics also include cytotoxic agents such as, for example, the pteridine family of drugs, diynenes, and the podophyllotoxins. Particularly useful members of those classes include, for example, methopterin, podophyllotoxin, or podophyllotoxin derivatives such as etoposide or etoposide phosphate, leurosidine, vindesine, leurosine and the like.

Still other cytotoxins that are compatible with the teachings herein include auristatins (e.g. auristatin E and monomethylauristan E), calicheamicin, gramicidin D, maytansanoids (e.g. maytansine), neocarzinostatin, topotecan, taxanes, cytochalasin B, ethidium bromide, emetine, tenoposide, colchicin, dihydroxy anthracindione, mitoxantrone, procaine, tetracaine, lidocaine, propranolol, puromycin, and analogs or homologs thereof.

Other types of functional moieties are known in the art and can be readily used in the methods and compositions of the present invention based on the teachings contained herein.

3.2. Chemistries for Linking Functional Moieties to Amino Acid Side Chains

Chemistries for linking the foregoing functional moieties be they small molecules, nucleic acids, polymers, peptides, proteins, chemotherapeutics, or other types of molecules to particular amino acid side chains are known in the art (for a detailed review of specific linkers see, for example, Hermanson, G. T., Bioconjugate Techniques, Academic Press (1996)).

Exemplary art recognized linking groups for sulfhydryl moieties (e.g., cysteine, or thiol side chain chemistries) include, but are not limited to, activated acyl groups (e.g., alpha-haloacetates, chloroacetic acid, or chloroacetamide), activated alkyl groups, Michael acceptors such as maleimide or acrylic groups, groups which react with sulfhydryl moieties via redox reactions, and activated di-sulfide groups. The sulfhydryl moieties may also be linked by reaction with bromotrifluoroacetone, alpha-bromo-beta-(5-imidazoyl)propionic acid, chloroacetyl phosphate, N-alkylmaleimides, 3-nitro-2-pyridyl disulfide, methyl-2-pyridyl disulfide, p-chloromercuribenzoate, 2-chloromercuri-4-nitrophenol, or chloro-7-nitrobenzo-2-oxa-1,3-diazole.

In a preferred embodiment, the cysteine or thiol side chain chemistry is linked during or subsequent to the production of an Fc containing polypeptide. For example, when producing the modified Fc containing polypeptide using cell culture, conditions are provided such that a free cysteine in solution can form a cysteine adduct with the thiol side chain of the Fc containing polypeptide. The so formed adduct may be used to inhibit glycosylation and/or effector function, or, subsequently subjected to reducing conditions to remove the adduct and thereby allow for the use of one of the aforementioned sulfhydryl chemistries.

Exemplary art recognized linking groups for hydroxyl moieties (e.g., serine, threonine, or tyrosine side chain chemistries) include those described above for sulfhydryl moieties including activated acyl groups, activated alkyl groups, and Michael acceptors.

Exemplary art recognized linking groups for amine moieties (e.g., asparagine or arginine side chain chemistries) include, but are not limited to, N-succinimidyl, N-sulfosuccinimidyl, N-phthalimidyl, N-sulfophthalimidyl, 2-nitrophenyl, 4-nitrophenyl, 2,4-dinitrophenyl, 3-sulfonyl-4-nitrophenyl, 3-carboxy-4-nitrophenyl, imidoesters (e.g., methyl picolinimidate), pyridoxal phosphate, pyridoxal, chloroborohydride, trinitrobenzenesulfonic acid, O-methyliosurea, and 2,4-pentanedione.

Exemplary art recognized linking groups for acidic moieties (e.g., aspartic acid or glutamic side chain chemistries) include activated esters and activated carbonyls. Acidic moieties can also be selectively modified by reaction with carbodiimides (R'N—C—N—R') such as 1-cyclohexyl-3-[2-morpholinyl-(4-ethyl)]carbodiimide or 1-ethyl-3-(4-azonia-4,4-dimethylpentyl)carbodiimide.

Where the functional moiety desired is a pegylation moiety, pegylation reactions known in the art are employed or as described herein (see also, e.g., Example 3). For example, in one method, the pegylation is carried out via an acylation reaction or an alkylation reaction with a reactive polyethylene glycol molecule (or an analogous reactive water-soluble polymer). A water-soluble polymer for pegylation of the antibodies and antibody fragments of the invention is polyethylene glycol (PEG). In another embodiment, the polymer for pegylation is polyethylene glycol-maleimide (i.e., PEG-maleimide).

Methods for preparing pegylated antibodies and antibody fragments of the invention will generally comprise the steps of a) reacting the antibody or antibody fragment with polyethylene glycol, such as a reactive ester or aldehyde derivative of PEG, under conditions whereby the antibody or antibody fragment becomes attached to one or more PEG groups, and b) obtaining the reaction products. It will be apparent to one of ordinary skill in the art to select the optimal reaction conditions or the acylation reactions based on known parameters and the desired result. In one embodiment, a particular amino acid reside can be targeted, for example, the first amino acid residue altered in order to inhibit glycosylation of a second amino acid residue, and preferably where the first amino acid is a cysteine or has a thiol chemistry.

4. Expression of Recombinant Antibodies

The modified antibodies of the invention are typically produced by recombinant expression. Nucleic acids encoding light and heavy chain variable regions, optionally linked to constant regions, are inserted into expression vectors. The light and heavy chains can be cloned in the same or different expression vectors. The DNA segments encoding immunoglobulin chains are operably linked to control sequences in the expression vector(s) that ensure the expression of immunoglobulin polypeptides. Expression control sequences include, but are not limited to, promoters (e.g., naturally-associated or heterologous promoters), signal sequences, enhancer elements, and transcription termination sequences. Preferably, the expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the crossreacting antibodies.

These expression vectors are typically replicable in the host organisms either as episomes or as an integral part of the host chromosomal DNA. Commonly, expression vectors contain selection markers (e.g., ampicillin-resistance, hygromycin-resistance, tetracycline resistance or neomycin resistance) to permit detection of those cells transformed with the desired DNA sequences (see, e.g., Itakura et al., U.S. Pat. No. 4,704,362).

*E. coli* is one prokaryotic host particularly useful for cloning the polynucleotides (e.g., DNA sequences) of the present invention. Other microbial hosts suitable for use include bacilli, such as *Bacillus subtilus*, and other enterobacteriaceae, such as *Salmonella, Serratia*, and various *Pseudomonas* species.

Other microbes, such as yeast, are also useful for expression. *Saccharomyces* and *Pichia* are exemplary yeast hosts, with suitable vectors having expression control sequences (e.g., promoters), an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for methanol, maltose, and galactose utilization.

In addition to microorganisms, mammalian tissue culture may also be used to express and produce the polypeptides of the present invention (e.g., polynucleotides encoding immunoglobulins or fragments thereof). See Winnacker, From Genes to Clones, VCH Publishers, N.Y., N.Y. (1987). Eukaryotic cells are actually preferred, because a number of suitable host cell lines capable of secreting heterologous proteins (e.g., intact immunoglobulins) have been developed in the art, and include CHO cell lines, various COS cell lines, HeLa cells, 293 cells, myeloma cell lines, transformed B-cells, and hybridomas. Expression vectors for these cells can include expression control sequences, such as an origin of replication, a promoter, and an enhancer (Queen et al., *Immunol. Rev.* 89:49 (1986)), and necessary processing information sites, such as ribosome binding sites, RNA splice sites, polyadenylation sites, and transcriptional terminator sequences. Preferred expression control sequences are promoters derived from immunoglobulin genes, SV40, adenovirus, bovine papilloma virus, cytomegalovirus and the like. See Co et al., *J. Immunol.* 148:1149 (1992).

Alternatively, antibody-coding sequences can be incorporated in transgenes for introduction into the genome of a transgenic animal and subsequent expression in the milk of the transgenic animal (see, e.g., Deboer et al., U.S. Pat. No. 5,741,957, Rosen, U.S. Pat. No. 5,304,489, and Meade et al., U.S. Pat. No. 5,849,992). Suitable transgenes include coding sequences for light and/or heavy chains in operable linkage with a promoter and enhancer from a mammary gland specific gene, such as casein or beta lactoglobulin.

The vectors containing the polynucleotide sequences of interest (e.g., the heavy and light chain encoding sequences and expression control sequences) can be transferred into the host cell by well-known methods, which vary depending on the type of cellular host. For example, calcium chloride transfection is commonly utilized for prokaryotic cells, whereas calcium phosphate treatment, electroporation, lipofection, biolistics or viral-based transfection may be used for other cellular hosts. (See generally Sambrook et al., *Molecular Cloning: A Laboratory Manual* (Cold Spring Harbor Press, 2nd ed., 1989). Other methods used to transform mammalian cells include the use of polybrene, protoplast fusion, liposomes, electroporation, and microinjection (see generally, Sambrook et al., supra). For production of transgenic animals, transgenes can be microinjected into fertilized oocytes, or can be incorporated into the genome of embryonic stem cells, and the nuclei of such cells transferred into enucleated oocytes.

The antibodies of the invention can be expressed using a single vector or two vectors. When the antibody heavy and light chains are cloned on separate expression vectors, the vectors are co-transfected to obtain expression and assembly of intact immunoglobulins. Once expressed, the whole antibodies, their dimers, individual light and heavy chains, or other immunoglobulin forms of the present invention can be purified according to standard procedures of the art, including ammonium sulfate precipitation, affinity columns, column chromatography, HPLC purification, gel electrophoresis and the like (see generally Scopes, Protein Purification (Springer-Verlag, N.Y., (1982)). Substantially pure immunoglobulins of at least about 90 to 95% homogeneity are preferred, and 98 to 99% or more homogeneity most preferred, for pharmaceutical uses.

5. Prophylactic, Diagnostic, and Therapeutic Methods

The present invention is also directed inter alia to the production of aglycosylated antibodies suitable for the prognosis, diagnosis, or treatment of diseases associated with immune disorders, including for example, disorders where it is desirable to bind an antigen using a therapeutic antibody but refrain from triggering effector function.

Accordingly, in certain embodiments, the aglycosylated antibodies or antigen-binding fragments of the present invention are useful in the prevention or treatment of immune disorders including, for example, glomerulonephritis, scleroderma, cirrhosis, multiple sclerosis, lupus nephritis, atherosclerosis, inflammatory bowel diseases or rheumatoid arthritis. In another embodiment, the antibodies or antigen-binding fragments of the invention can be used to treat or prevent inflammatory disorders, including, but not limited to, Alzheimer's, severe asthma, atopic dermatitis, cachexia, CHF-ischemia, coronary restinosis, Crohn's disease, diabetic nephropathy, lymphoma, psoriasis, fibrosis/radiation-induced, juvenile arthritis, stroke, inflammation of the brain or central nervous system caused by trauma, and ulcerative colitis.

Other inflammatory disorders which can be prevented or treated with the aglycosylated antibodies or antigen-binding fragments of the invention include inflammation due to corneal transplantation, chronic obstructive pulmonary disease, hepatitis C, multiple myeloma, and osteoarthritis.

In another embodiment, the antibodies or Fc-containing fragments of the invention can be used to prevent or treat neoplasia, including, but not limited to bladder cancer, breast cancer, head and neck cancer, Kaposi's sarcoma, melanoma, ovarian cancer, small cell lung cancer, stomach cancer, leukemia/lymphoma, and multiple myeloma. Additional neoplasia conditions include, cervical cancer, colo-rectal cancer, endometrial cancer, kidney cancer, non-squamous cell lung cancer, and prostate cancer.

In another embodiment, the antibodies or antigen-binding fragments of the invention can be used to prevent or treat neurodegenerative disorders, including, but not limited to Alzheimer's, stroke, and traumatic brain or central nervous system injuries. Additional neurodegenerative disorders include ALS/motor neuron disease, diabetic peripheral neuropathy, diabetic retinopathy, Huntington's disease, macular degeneration, and Parkinson's disease.

In still another embodiment, the antibody or Fc-containing fragment of the invention an be used to prevent or treat an infection caused by a pathogen, for example, a virus, prokaryotic organism, or eukaryotic organism.

In clinical applications, a subject is identified as having or at risk of developing one of the above-mentioned conditions by exhibiting at least one sign or symptom of the disease or disorder. At least one antibody or antigen-binding fragment thereof of the invention or compositions comprising at least one antibody or antigen-binding fragment thereof of the invention is administered in a sufficient amount to treat at least one symptom of a disease or disorder, for example, as mentioned above. In one embodiment, a subject is identified as exhibiting at least one sign or symptom of a disease or disorder associated with detrimental CD154 activity (also known as CD40 ligand or CD40L; see, e.g., Yamada et al., Transplantation, 73:S36-9 (2002); Schonbeck et al., Cell. Mol. Life Sci. 58:4-43 (2001); Kirk et al., Philos. Trans. R. Soc. Lond. B. Sci. 356:691-702 (2001); Fiumara et al., Br. J. Haematol. 113:265-74 (2001); and Biancone et al., Int. J. Mol. Med. 3(4):343-53 (1999)).

Accordingly, an aglycosylated antibody of the invention is suitable for administration as a therapeutic immunological reagent to a subject under conditions that generate a beneficial therapeutic response in a subject, for example, for the prevention or treatment of a disease or disorder, as for example, described herein.

Therapeutic agents of the invention are typically substantially pure from undesired contaminant. This means that an agent is typically at least about 50% w/w (weight/weight) purity, as well as being substantially free from interfering proteins and contaminants. Sometimes the agents are at least about 80% w/w and, more preferably at least 90 or about 95% w/w purity. However, using conventional protein purification techniques, for example as described herein, homogeneous peptides of at least 99% W/w can be obtained.

The methods can be used on both asymptomatic subjects and those currently showing symptoms of disease. The antibodies used in such methods can be human, humanized, chimeric or nonhuman antibodies, or fragments thereof (e.g., antigen binding fragments) and can be monoclonal or polyclonal.

In another aspect, the invention features administering an antibody with a pharmaceutical carrier as a pharmaceutical composition. Alternatively, the antibody can be administered to a subject by administering a polynucleotide encoding at least one antibody chain. The polynucleotide is expressed to produce the antibody chain in the subject. Optionally, the polynucleotide encodes heavy and light chains of the antibody. The polynucleotide is expressed to produce the heavy and light chains in the subject. In exemplary embodiments, the subject is monitored for the level of administered antibody in the blood of the subject.

The invention thus fulfills a longstanding need for therapeutic regimes for preventing or ameliorating immune conditions, for example, CD154-associated immune conditions.

It is also understood the antibodies of the invention are suitable for diagnostic or research applications, especially, for example, an diagnostic or research application comprising a cell-based assay where reduced effector function is desirable.

6. Animal Models for Testing the Efficacy of Aglycosylated Antibodies

An antibody of the invention can be administered to a non-human mammal in need of, for example, an aglycosylated antibody therapy, either for veterinary purposes or as an animal model of human disease, e.g., an immune disease or condition stated above. Regarding the latter, such animal models may be useful for evaluating the therapeutic efficacy of antibodies of the invention (e.g., testing of effector function, dosages, and time courses of administration).

Examples of animal models which can be used for evaluating the therapeutic efficacy of antibodies or antigen-binding fragments of the invention for preventing or treating rheumatoid arthritis (RA) include adjuvant-induced RA, collagen-induced RA, and collagen mAb-induced RA (Holmdahl et al., (2001) *Immunol. Rev.* 184:184; Holmdahl et al., (2002) *Ageing Res. Rev.* 1:135; Van den Berg (2002) *Curr. Rheumatol. Rep.* 4:232).

Examples of animal models which can be used for evaluating the therapeutic efficacy of antibodies or antigen-binding fragments of the invention for preventing or treating inflammatory bowel disease (IBD) include TNBS-induced IBD, DSS-induced IBD, and (Padol et al. (2000) *Eur. J. Gastrolenterol. Hepatol.* 12:257; Murthy et al. (1993) *Dig. Dis. Sci.* 38:1722).

Examples of animal models which can be used for evaluating the therapeutic efficacy of antibodies or antigen-binding fragments of the invention for preventing or treating glomerulonephritis include anti-GBM-induced glomerulonephritis (Wada et al. (1996) *Kidney Int.* 49:761-767) and anti-thyl-induced glomerulonephritis (Schneider et al. (1999) *Kidney Int.* 56:135-144).

Examples of animal models which can be used for evaluating the therapeutic efficacy of antibodies or antigen-binding fragments of the invention for preventing or treating multiple sclerosis include experimental autoimmune encephalomyelitis (EAE) (Link and Xiao (2001) *Immunol. Rev.* 184:117-128).

Animal models can also be used for evaluating the therapeutic efficacy of antibodies or antigen-binding fragments of the invention for preventing or treating CD154-related conditions, such as systemic erythematosus lupus (SLE), for example using the MRL-Fas$^{lpr}$ mice (Schneider, supra; Tesch et al. (1999) *J. Exp. Med.* 190).

7. Treatment Regimes and Dosages

In prophylactic applications, pharmaceutical compositions or medicaments are administered to a subject suffering from a disorder treatable with a polypeptide having an Fc region, for example, an immune system disorder, in an amount sufficient to eliminate or reduce the risk, lessen the severity, or delay the outset of the disorder, including biochemical, histologic and/or behavioral symptoms of the disorder, its complications and intermediate pathological phenotypes presenting during development of the disorder. In therapeutic applications, compositions or medicaments are administered to a subject suspected of, or already suffering from such a disorder in an amount sufficient to cure, or at least partially arrest, the symptoms of the disorder (biochemical, histologic and/or behavioral), including its complications and intermediate pathological phenotypes in development of the disorder. The polypeptides of the invention are particularly useful for modulating the biological activity of a cell surface antigen that resides in the blood, where the disease being treated or prevented is caused at least in part by abnormally high or low biological activity of the antigen.

In some methods, administration of agent reduces or eliminates the immune disorder, for example, inflammation, such as associated with CD154 activity. An amount adequate to accomplish therapeutic or prophylactic treatment is defined as a therapeutically- or prophylactically-effective dose. In both prophylactic and therapeutic regimes, agents are usually administered in several dosages until a sufficient immune response has been achieved.

Effective doses of the compositions of the present invention, for the treatment of the above described conditions vary depending upon many different factors, including means of administration, target site, physiological state of the subject, whether the subject is human or an animal, other medications administered, and whether treatment is prophylactic or therapeutic. Usually, the subject is a human but non-human mammals including transgenic mammals can also be treated.

For passive immunization with an antibody, the dosage ranges from about 0.0001 to 100 mg/kg, and more usually 0.01 to 20 mg/kg, of the host body weight. For example dosages can be 1 mg/kg body weight or 10 mg/kg body weight or within the range of 1-10 mg/kg, preferably at least 1 mg/kg. Subjects can be administered such doses daily, on alternative days, weekly or according to any other schedule determined by empirical analysis. An exemplary treatment entails administration in multiple dosages over a prolonged period, for example, of at least six months. Additional exemplary treatment regimes entail administration once per every two weeks or once a month or once every 3 to 6 months. Exemplary dosage schedules include 1-10 mg/kg or 15 mg/kg on consecutive days, 30 mg/kg on alternate days or 60 mg/kg weekly. In some methods, two or more monoclonal antibodies with different binding specificities are administered simultaneously, in which case the dosage of each antibody administered falls within the ranges indicated.

Antibody is usually administered on multiple occasions. Intervals between single dosages can be weekly, monthly or yearly. In some methods, dosage is adjusted to achieve a plasma antibody concentration of 1-1000 μg/ml and in some methods 25-300 μg/ml. Alternatively, antibody can be administered as a sustained release formulation, in which case less frequent administration is required. Dosage and frequency vary depending on the half-life of the antibody in the subject. In general, human antibodies show the longest half-life, followed by humanized antibodies, chimeric antibodies, and nonhuman antibodies.

The dosage and frequency of administration can vary depending on whether the treatment is prophylactic or therapeutic. In prophylactic applications, compositions containing the present antibodies or a cocktail thereof are administered to a subject not already in the disease state to enhance the subject's resistance. Such an amount is defined to be a "prophylactic effective dose." In this use, the precise amounts again depend upon the subject's state of health and general immunity, but generally range from 0.1 to 25 mg per dose, especially 0.5 to 2.5 mg per dose. A relatively low dosage is administered at relatively infrequent intervals over a long period of time. Some subjects continue to receive treatment for the rest of their lives.

In therapeutic applications, a relatively high dosage (e.g., from about 1 to 200 mg of antibody per dose, with dosages of from 5 to 25 mg being more commonly used) at relatively short intervals is sometimes required until progression of the disease is reduced or terminated, and preferably until the subject shows partial or complete amelioration of symptoms of disease. Thereafter, the patent can be administered a prophylactic regime.

Doses for nucleic acids encoding antibodies range from about 10 ng to 1 g, 100 ng to 100 mg, 1 μg to 10 mg, or 30-300 μg DNA per subject. Doses for infectious viral vectors vary from 10-100, or more, virions per dose.

Therapeutic agents can be administered by parenteral, topical, intravenous, oral, subcutaneous, intraarterial, intracranial, intraperitoneal, intranasal or intramuscular means for prophylactic and/or therapeutic treatment. The most typical route of administration of a protein drug is intravascular, subcutaneous, or intramuscular, although other routes can be effective. In some methods, agents are injected directly into a particular tissue where deposits have accumulated, for example intracranial injection. In some methods, antibodies are administered as a sustained release composition or device, such as a Medipad™ device. The protein drug can also be administered via the respiratory tract, e.g., using a dry powder inhalation device.

Agents of the invention can optionally be administered in combination with other agents that are at least partly effective in treatment of immune disorders.

8. Pharmaceutical Compositions

The therapeutic compositions of the invention include at least one aglycosylated antibody or antibody fragment of the invention in a pharmaceutically acceptable carrier. A "pharmaceutically acceptable carrier" refers to at least one component of a pharmaceutical preparation that is normally used for administration of active ingredients. As such, a carrier may contain any pharmaceutical excipient used in the art and any form of vehicle for administration. The compositions may be, for example, injectable solutions, aqueous suspensions or solutions, non-aqueous suspensions or solutions, solid and liquid oral formulations, salves, gels, ointments, intradermal patches, creams, lotions, tablets, capsules, sustained release formulations, and the like. Additional excipients may include, for example, colorants, taste-masking agents, solubility aids, suspension agents, compressing agents, enteric coatings, sustained release aids, and the like.

Agents of the invention are often administered as pharmaceutical compositions comprising an active therapeutic agent, i.e., and a variety of other pharmaceutically acceptable components. See Remington's Pharmaceutical Science (15th ed., Mack Publishing Company, Easton, Pa. (1980)). The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

Antibodies can be administered in the form of a depot injection or implant preparation, which can be formulated in such a manner as to permit a sustained release of the active ingredient. An exemplary composition comprises monoclonal antibody at 5 mg/mL, formulated in aqueous buffer consisting of 50 mM L-histidine, 150 mM NaCl, adjusted to pH 6.0 with HCl.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above (see Langer, Science 249: 1527 (1990) and Hanes, Advanced Drug Delivery Reviews 28:97 (1997)).

9. Monitoring the Course of Treatment

Treatment of a subject suffering from a disease or disorder, such as an immune disorder, can be monitored using standard methods. Some methods entail determining a baseline value, for example, of an antibody level or profile in a subject, before administering a dosage of agent, and comparing this with a value for the profile or level after treatment. A significant increase (i.e., greater than the typical margin of experimental error in repeat measurements of the same sample, expressed as one standard deviation from the mean of such measurements) in value of the level or profile signals a positive treatment outcome (i.e., that administration of the agent has achieved a desired response). If the value for immune response does not change significantly, or decreases, a negative treatment outcome is indicated.

In other methods, a control value (i.e., a mean and standard deviation) of level or profile is determined for a control population. Typically the individuals in the control population have not received prior treatment. Measured values of the level or profile in a subject after administering a therapeutic agent are then compared with the control value. A significant increase relative to the control value (e.g., greater than one standard deviation from the mean) signals a positive or sufficient treatment outcome. A lack of significant increase or a decrease signals a negative or insufficient treatment outcome. Administration of agent is generally continued while the level is increasing relative to the control value. As before, attainment of a plateau relative to control values is an indicator that the administration of treatment can be discontinued or reduced in dosage and/or frequency.

In other methods, a control value of the level or profile (e.g., a mean and standard deviation) is determined from a control population of individuals who have undergone treatment with a therapeutic agent and whose levels or profiles have plateaued in response to treatment. Measured values of levels or profiles in a subject are compared with the control value. If the measured level in a subject is not significantly different (e.g., more than one standard deviation) from the control value, treatment can be discontinued. If the level in a subject is significantly below the control value, continued administration of agent is warranted. If the level in the subject persists below the control value, then a change in treatment may be indicated.

In other methods, a subject who is not presently receiving treatment but has undergone a previous course of treatment is monitored for antibody levels or profiles to determine whether a resumption of treatment is required. The measured level or profile in the subject can be compared with a value previously achieved in the subject after a previous course of treatment. A significant decrease relative to the previous measurement (i.e., greater than a typical margin of error in repeat measurements of the same sample) is an indication that treatment can be resumed. Alternatively, the value measured in a subject can be compared with a control value (mean plus standard deviation) determined in a population of subjects after undergoing a course of treatment. Alternatively, the measured value in a subject can be compared with a control value in populations of prophylactically treated subjects who remain free of symptoms of disease, or populations of therapeutically treated subjects who show amelioration of disease characteristics. In all of these cases, a significant decrease relative to the control level (i.e., more than a standard deviation) is an indicator that treatment should be resumed in a subject.

The antibody profile following administration typically shows an immediate peak in antibody concentration followed by an exponential decay. Without a further dosage, the decay approaches pretreatment levels within a period of days to months depending on the half-life of the antibody administered. For example the half-life of some human antibodies is of the order of 20 days.

In some methods, a baseline measurement of antibody to a given antigen in the subject is made before administration, a second measurement is made soon thereafter to determine the peak antibody level, and one or more further measurements are made at intervals to monitor decay of antibody levels. When the level of antibody has declined to baseline or a predetermined percentage of the peak less baseline (e.g., 50%, 25% or 10%), administration of a further dosage of antibody is administered. In some methods, peak or subsequent measured levels less background are compared with reference levels previously determined to constitute a beneficial prophylactic or therapeutic treatment regime in other subjects. If the measured antibody level is significantly less than a reference level (e.g., less than the mean minus one standard deviation of the reference value in population of subjects benefiting from treatment) administration of an additional dosage of antibody is indicated.

Additional methods include monitoring, over the course of treatment, any art-recognized physiologic symptom (e.g., physical or mental symptom) routinely relied on by researchers or physicians to diagnose or monitor disorders.

The following examples are included for purposes of illustration and should not be construed as limiting the invention.

EXEMPLIFICATION

Throughout the examples, the following materials and methods were used unless otherwise stated.

Materials and Methods

In general, the practice of the present invention employs, unless otherwise indicated, conventional techniques of chemistry, molecular biology, recombinant DNA technology, immunology (especially, e.g., antibody technology), and standard techniques in electrophoresis. See, e.g., Sambrook, Fritsch and Maniatis, Molecular Cloning: Cold Spring Harbor Laboratory Press (1989); Antibody Engineering Protocols (Methods in Molecular Biology), 510, Paul, S., Humana Pr (1996); Antibody Engineering: A Practical Approach (Practical Approach Series, 169), McCafferty, Ed., Irl Pr (1996); Antibodies: A Laboratory Manual, Harlow et al., C.S.H.L. Press, Pub. (1999); and Current Protocols in Molecular Biology, eds. Ausubel et al., John Wiley & Sons (1992).

Production of the Modified Antibodies

For producing the modified antibodies of the invention, polynucleotides encoding either a model human antibody (hu5c8), variant antibodies thereof, or corresponding Fc regions, were introduced into standard expression vectors. The human antibody hu5c8 and variants thereof are described in, e.g., U.S. Pat. Nos. 5,474,771 and 6,331,615. The cDNA sequence and amino acid sequence are provided in the sequence listing for, respectively, the hu5c8 IgG1 heavy chain (SEQ ID NOS: 1-2), hu5c8 light chain (SEQ ID NOS: 3-4), hu5c8 IgG1 Fc region (SEQ ID NOS: 5-6), hu5C8 IgG4 heavy chain (SEQ ID NOS: 7-8), hu5c8 IgG4 variant (S228P) (SEQ ID NOS: 9-10), and hu5c8 IgG4 variant (S228P/T299A) (SEQ ID NOS: 11-12). Vectors where then introduced into EBNA 293 cells using large-scale transient transfection techniques. The transfected 293 cells were cultured using standard media and incubation conditions. Cells were typically refed after 1 day post-transfection and then allowed to express and secrete the recombinant protein for 1 to 3 days. Culture media containing the secreted recombinant antibodies or Fc regions were then harvested for purification.

Purification of the Modified Antibodies

For performing antibody purification, recombinant aglycosylated antibodies produced in eukaryotic cells were harvested from the cell culture medium and subjected to the following chromatography techniques. In particular, recombinant Protein A columns (5 mL) were prepared and washed with 100 mL 0.1 N NaOH and then equilibrated with PBS until neutralized. The conditioned media (~1.5 L) was then pumped through the column at 10 mL/min. After loading, the column was washed with 100 mL 3×PBS and then 10 mL 1×PBS. The antibodies were eluted with 1.3 mL fractions of 100 mM NaH$_2$PO$_4$, pH 2.8 into collection tubes containing 0.3 mL 1 M HEPES, pH 8 for immediate neutralization. Fractions containing the eluted antibodies were identified by monitoring the concentration using light absorbance (A280) of 1:10 dilutions of each fraction. This purification step was scaled up or down proportionately to the scale of the transient transfection.

Resultant Protein A pools were further purified by chromatography on a 1.6 mL Poros HS column. The recombinant protein pools (~8 mL) were diluted ten-fold with 25 mM NaAcetate, pH 4.5 and half was loaded in each of two purification runs using a BioCad HPLC. The proteins were loaded at a flow rate of 5 mL/min, the column washed with 10 column volumes of the dilution buffer and then eluted with a 25 column volume gradient of 0 to 1 M NaCl in the dilution buffer. Fractions of 0.8 mL were collected and monitored for protein concentration by light absorbance (A280).

Alternatively, the resultant Protein A pool from a small scale preparation was purified by Protein L chromatography. A Protein L column (1 mL) was prepared and washed with 10 mL 0.1 N NaOH and then equilibrated with PBS until neutralized. The neutralized Protein A pool (3 mL) was then loaded in 1 mL aliquots. After loading, the column was washed with 10 mL 3×PBS and then 10 mL 1×PBS. The antibodies were eluted with 0.4 mL fractions of 100 mM NaH$_2$PO$_4$, pH 2.8 into collection tubes containing 0.1 mL 1 M HEPES, pH 8 for immediate neutralization. Fractions containing the eluted antibodies were identified by monitoring the concentration using light absorbance (A280) of 1:5 dilutions of each fraction.

In addition to light absorbance, eluants containing recombinant protein were also monitored with a refractive index detector (Waters) and a Precision Detector PD2020 light scattering instrument. Molecular weights were calculated with the Precision Detector software. All variant antibodies (four forms of hu5c8) eluted identically from the SEC column, showing a single major peak with a minor amount of higher molecular weight material (dimer). A molecular weight of 148,300 was determined by light scattering for the main peak of the T299C hu5c8 variant. Size exclusion chromatography of the huIgG1 Fc variants was carried out identically to the full length antibodies. All four Fc proteins ran identically, giving a major peak with calculated MWs ranging from 53,000 to 55,000 Daltons. Finally, recombinant protein samples were obtained, dialyzed against PBS, sterile filtered, and stored at 4° C. in 10 mg aliquots until needed for further analysis.

SDS-PAGE

For performing SDS-PAGE, protein samples were typically diluted to 200 µg/mL in Laemmli SDS-PAGE sample buffer containing either 25 mM DTT for reducing conditions, or 25 mM NEM for non-reducing conditions. Aliquots of 2.5 and 10 µl were loaded on 4-20% gradient gels.

Mass Spectrometry

For performing mass spectroscopy, protein samples were reduced in 9 mM DTT, at pH 7.8, prior to analysis. The samples were desalted over a C4 guard column and analyzed on-line by ESMS using a triple quadrupole instrument. The ESMS raw data were deconvoluted by the MaxEnt program to generate zero charged mass spectra. This procedure allows for multiple charged signals to collapse into one peak for molecular mass determinations.

Pegylation

For performing pegylation of the aglycosylated polypeptides of the invention, aliquots of 50 µL of 0.94 mg/mL solutions of the T299A and T299C variant Fc were first precipitated with 1 mL ethanol at −20° C. overnight. Resultant precipitates were then pelleted and the ethanol removed and 50 µL of a solution of 6.4 M urea, 2% SDS and 10 mM EDTA, pH 8 was added and the solution heated to 100° C. for 5 min. For reduction, half the samples were treated with 4 mM TCEP for 30 min at room temperature. Aliquots of 5 µL of 1 M MES buffer at pH 6.5 were then added followed by either 50 µL H2O or a 5 mM solution of PEG (5K)-maleimide. After 30 min at room temperature, 10 µL aliquots of a 4× solution of Laemmli SDS-PAGE sample buffer was added to 30 µL of the reaction mixtures and the solution heated to 100° C. for 5 min. Then 5 and 15 µL aliquots of recombinant protein were loaded on 4-20% gradient gels for a determination of relative amounts of pegylation that occurred.

Example 1

Methods for Producing and Characterizing Aglycosylated Antibodies

The following example describes the production of an aglycosylated antibody in a eukaryotic cell and the characterization of the resultant antibody.

Figure 3:
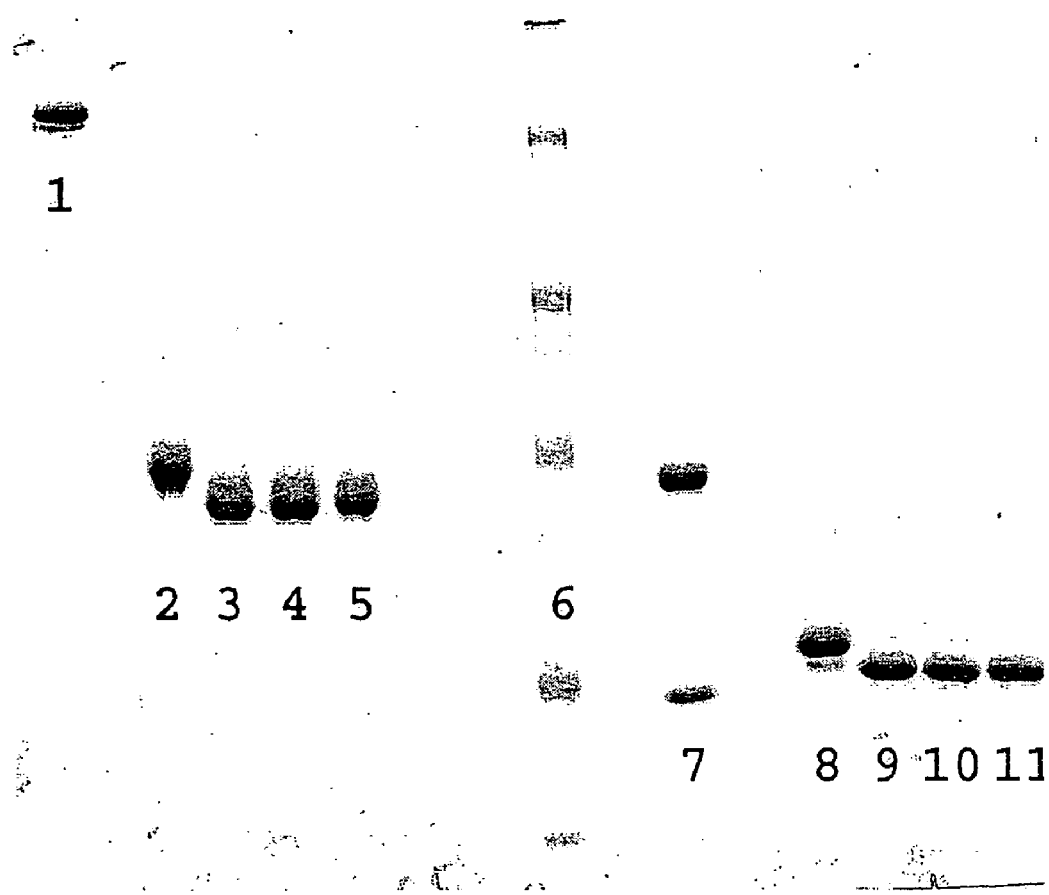
FIG. 3 depicts a digital image of SDS-PAGE analysis of glycosylated antibodies and aglycosylated antibody IgG1 variants under non-reducing conditions (lanes 1-5) and reducing conditions (lanes 7-11). The aglycosylated antibody variants (or Fc regions thereof) migrate faster than glycosylated controls because they lack the added sugar moieties (compare lanes 3-5 with lane 2 and lanes 9-11 with lane 8). In particular, lane 1 contains a control full length antibody (monoclonal IgG1), lane 2 contains a control wild type (glycosylated) Fc region (IgG1), lane 3 contains an aglycosylated Fc variant (N297Q human IgG1), lane 4 contains an aglycosylated Fc variant (T299A human IgG1), lane 5 contains an aglycosylated Fc variant (T299C human IgG1), lane 6 contains molecular weight standards, lane 7 contains a control full length antibody (monoclonal IgG1), lane 8, contains a control wild type (glycosylated) Fc region (IgG1), lane 9 contains an aglycosylated Fc variant (N297Q human IgG1), lane 10 contains an aglycosylated Fc variant (T299A human IgG1), and lane 11 contains an aglycosylated Fc variant (T299C human IgG1).
Figure 4:
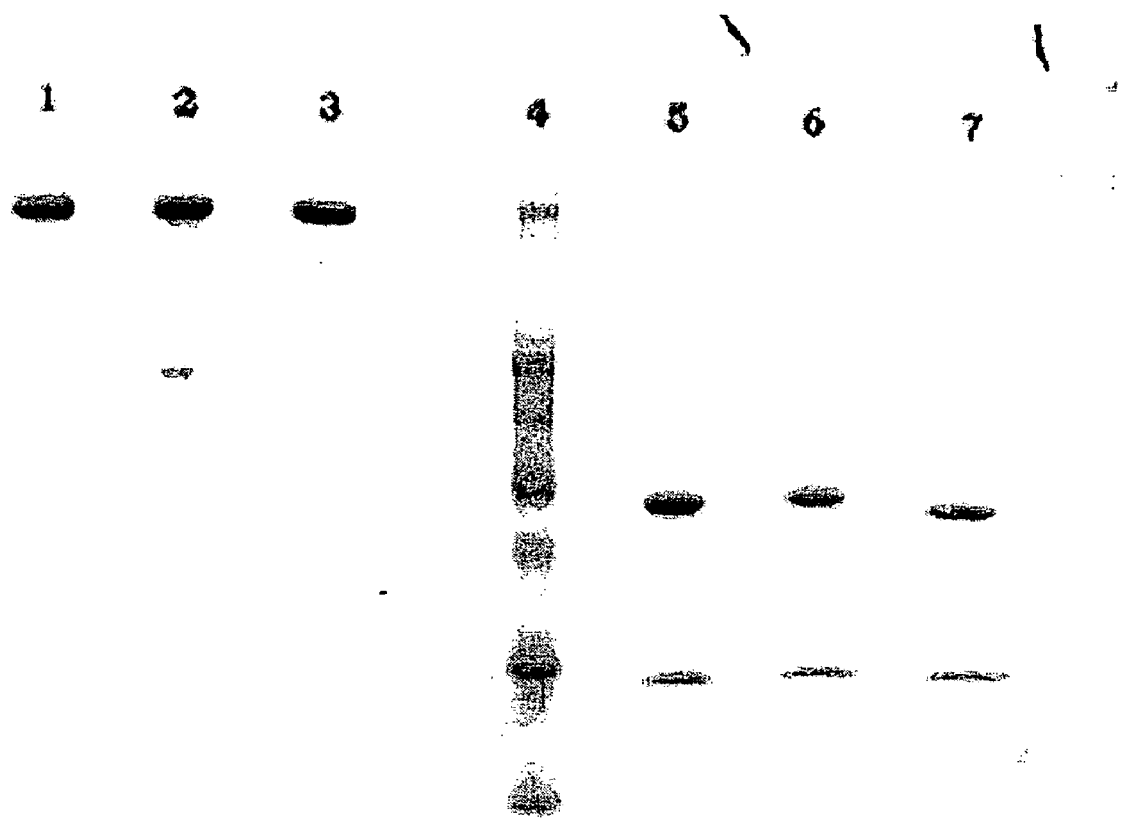
FIG. 4 depicts a digital image of SDS-PAGE analysis of glycosylated antibodies and aglycosyl antibody IgG4 variants under non-reducing conditions (lanes 1-3) and reducing conditions (lanes 5-7). The IgG4 aglycosyl antibody variant migrates faster than the glycosylated control because it lacks the added sugar moieties (compare lane 3 with lane 2 and lane 7 with lane 6). In particular, lanes 1 and 5 contain a control IgG1, lanes 2 and 6 contain a control IgG4 antibody, and lanes 3 and 7 contain the IgG4 aglycosyl variant (T299A). Lane 4 contains molecular weight standards.

Nucleic acids encoding a model human antibody (hu5c8) of the IgG1 subtype having binding affinity for the CD154 ligand were genetically engineered to have one of several alterations. The first alteration comprised a codon encoding in place of the wild type amino acid residue, i.e., threonine, at position 299, an alanine (T299A). In another alteration, the codon encoding threonine at position 299 was changed to encode a cysteine (T299A). A control alteration was also included, in which the specific asparagine that is glycosylated is mutated (N297Q) (FIGS. 3, 5-7). In addition, the T299A mutation was introduced into a model human antibody hu5C8 of the IgG4 subtype. The IgG4 sequence had a further modification in the hinge peptide (S228P) to stabilize the interchain disulfides, an issue unrelated to the aglycosyl modification (FIG. 4). Each alteration was incorporated into an expression vector and introduced into a eukaryotic cell line using the methods described herein. In addition, the forgoing alterations where also tested in the context of an Fc region unlinked from the corresponding variable region. Each modified antibody, or Fc fragment thereof, along with a corresponding control antibody or antibody fragment, was then expressed in cell culture, harvested from the cell culture media, and purified using standard techniques. Each antibody or antibody fragment was then characterized for its aglycosylation and binding activity.

The aglycosylation for each antibody or antibody fragment was characterized using standard gel electrophoresis and chromatography techniques. In particular, reducing and non-reducing SDS-PAGE and size exclusion chromatography under native conditions were performed and demonstrated that the T299A and T299C variants of test antibody (hu5c8) and fragments thereof, i.e., huIgG1 Fc, were of the expected molecular size and subunit organization. The absence of glycosylation of the T299A and T299C antibody variants was indicated by the more rapid migration of the heavy chain of the proteins on reducing SDS-PAGE (FIG. 3). In addition, mass spectrometry under reducing conditions confirmed the expected mass of the constructs and the absence of glycans in the T299A and T299C variants (FIGS. 8-11). Mass spectroscopy under non-reducing conditions also demonstrated the presence of cysteine adducts on the huIgG1 T299C Fc variants (FIGS. 8-11).

Figure 5:
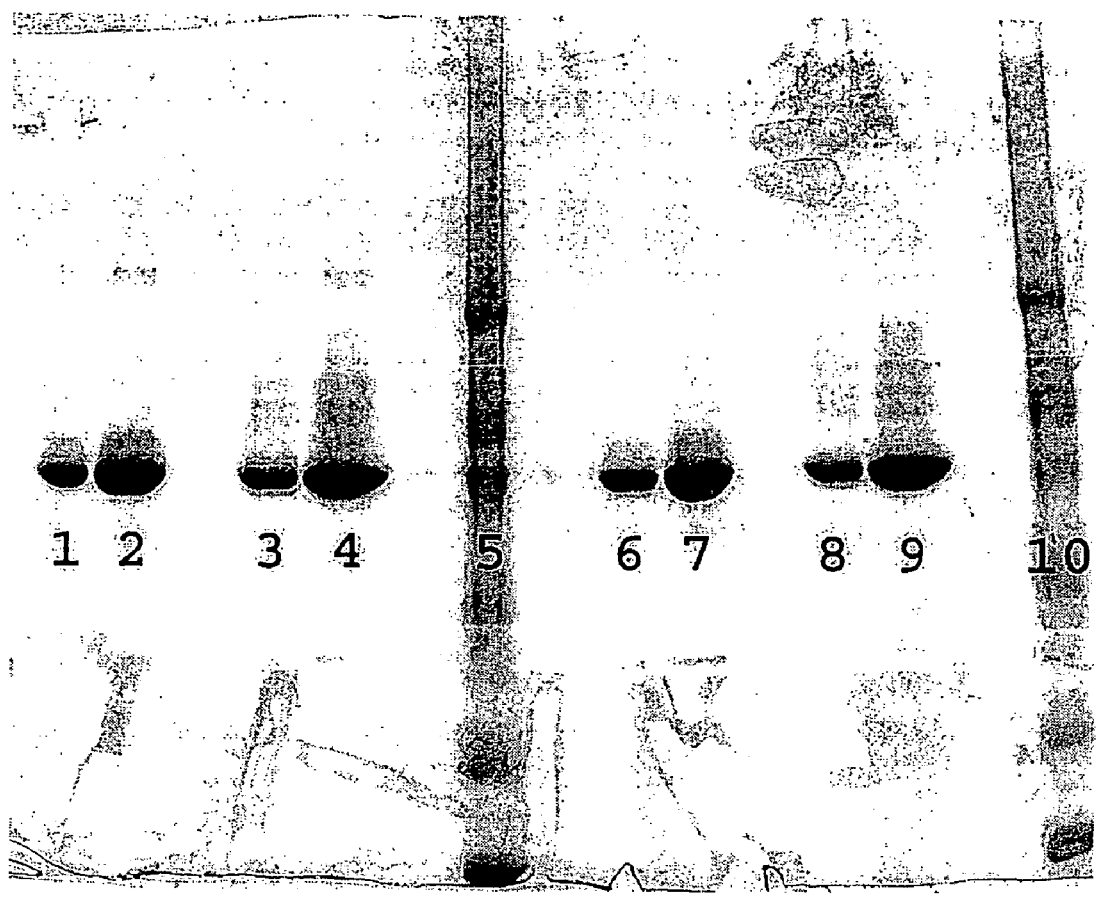
FIG. 5 depicts a digital image of SDS-PAGE analysis of aglycosylated antibody variants (Fc regions) under non-reducing conditions showing that cysteines are blocked in the presence (lanes 3, 4, 8, and 9) or absence (lanes 1, 2, 6, and 7) of peg-maleimide. In particular, lanes 1-4 contain T299C and lanes 6-9 contain T299A, with molecular weight standards in lane 10.

The mass of the T299A variant corresponded to the predicted protein dimer (expected, 51,824.7, found, 51,826). In contrast the mass of the T299C variant was 246 Daltons larger that predicted (expected 51,886, found 52,132) (FIG. 3). This would correspond to the addition of two cysteine adducts to the Fc dimer (2×120=240) (FIG. 5).

Accordingly, it was concluded that the alteration of the first amino acid proximal to a glycosylation motif inhibited the glycosylation of the antibody at second amino acid residue thereby providing an efficient and reliable approach for producing aglycosylated antibodies in eukaryotic cells.

Example 2

Methods for Producing an Aglycosylated Antibody with Reduced Effector Function Using Amino Acid Substitutions of Sufficient Steric Bulk and/or Charge The following example describes the production of an aglycosylated antibody by altering an antibody at a first amino acid residue with a residue that has sufficient steric bulk and/or charge as to inhibit glycosylation.

Nucleic acids encoding a candidate antibody, for example, an antibody of the IgG1 or IgG4 subtype, were genetically engineered to have one of several alterations predicted to inhibit glycosylation and/or effector function. While not wishing to be bound by theory, results obtained above for a cysteine adduct support the rationale that a sufficiently bulky and/or charged residue will inhibit a glycosidase from glycosylating an Fc-containing polypeptide and reduce undesired effector function. For example, a substitution at the Kabat position of 299 (e.g., T299) with a bulky or charged residue is predicted to inhibit a glycosidase from glycosylating the antibody at, for example, position 297. In addition, such an amino acid substitution is also predicted to modulate the binding of the antibody to an Fc receptor. In the bound complex between an antibody Fc region and an Fc receptor, for example, the FcγIIIb receptor, the residue T299 of the antibody Fc region is located very close to the binding interface with the FcγIIIb receptor. In particular, the distances of the side chain chemistry of the T299 residue to the Y150 and H152 residues of the FcγIIIb receptor are 4.2 Å and 5.6 Å, respectively. Thus, by substituting T299 for a residue with sufficient steric bulk, such as F, H, Q, W, or Y, the antibody will not only be aglycosylated but also have reduced Fc binding affinity to the Fc receptor due to unfavorable steric interactions.

Still further, the inhibition of glycosylation and Fc binding can be modulated by substituting T299 with a charged side chain chemistry such as D, E, K, or R. The resulting antibody variant will not only have reduced glycosylation but also reduced Fc binding affinity to an Fc receptor due to unfavorable electrostatic interactions.

Accordingly, modifying a first amino acid residue side chain chemistry to one of sufficient steric bulk and/or charge, is predicted to inhibit the glycosylation of the antibody at a second amino acid residue as well as reduce Fc binding to an Fc receptor. Thus, the invention provides an efficient and reliable approach for producing aglycosylated antibodies with reduced effector function in eukaryotic cells.

Example 3

Methods for Pegylating Aglycosylated Antibodies

The following example describes the production of an aglycosylated antibody in a eukaryotic cell and the pegylation of the resultant antibody.

Figure 6:
FIG. 6 depicts a digital image of SDS-PAGE analysis of aglycosylated antibody variants (Fc regions) under reducing conditions showing that introduced cysteines (T299C) are pegylated but alanine resides (T299A) are not, as evidenced by reduced mobility. In particular, lanes 1-2 were loaded with increasing amounts (2.5 ug, 7.5 ug) of Fc T299C, lanes 3-4 were loaded with pegylated Fc T299C, lanes 5-6 were loaded with increasing amounts of Fc T299A, lanes 7-8 were loaded with pegylated Fc T299A, and lane 9 was loaded with a protein molecular weight marker.

In particular, the T299C antibody variant was determined to be specifically modified with Peg-maleimide under non-denaturing conditions by first reducing the protein with TCEP to remove the cysteine adduct, allowing the hinge disulfides to reform by dialyzing the protein over several days, and reacting with PEG-maleimide. The T299A antibody variant could not be modified with PEG under these conditions (FIG. 6).

Figure 7:
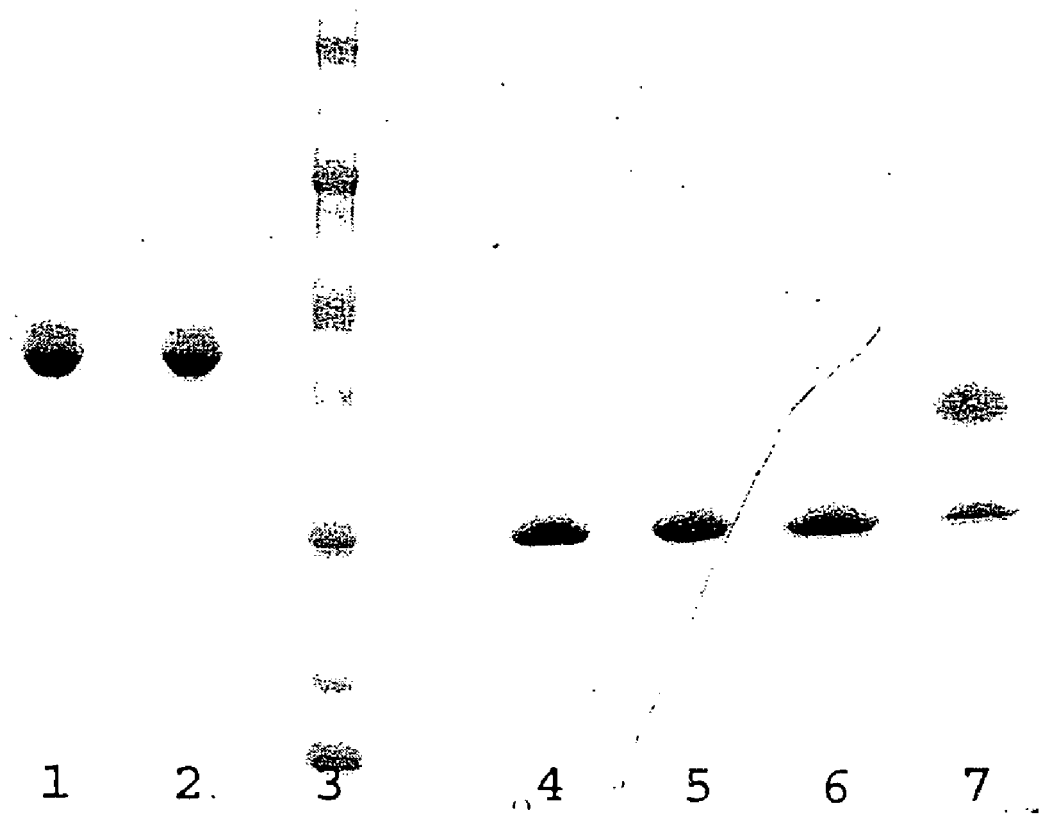
FIG. 7 depicts a digital image of SDS-PAGE analysis of the pegylation of the antibody variant T299C (Fc region) as compared to antibody variant T299A (Fc region) under non-reducing and non-denaturing conditions after first reducing the test proteins with TCEP to remove the cysteine adduct followed by pegylation showing that the introduced cysteines (T299C) are pegylated but alanine resides (T299A) are not, as evidenced by reduced mobility. In particular, lane 1 was loaded with Fc T299A after reduction and reoxidation, non-reducing gel conditions, lane 2 with Fc T299C after reduction and reoxidation, non-reducing gel conditions, lane 3 with a protein molecular weight marker, lane 4 Fc T299A with no peg-maleimide, reducing gel conditions, lane 5 Fc T299C no peg-maleimide, reducing gel conditions, lane 6 Fc T299A plus peg-maleimide, reducing gel conditions, and lane 7 with Fc T299C plus peg-maleimide, reducing gel conditions.
Figure 8:
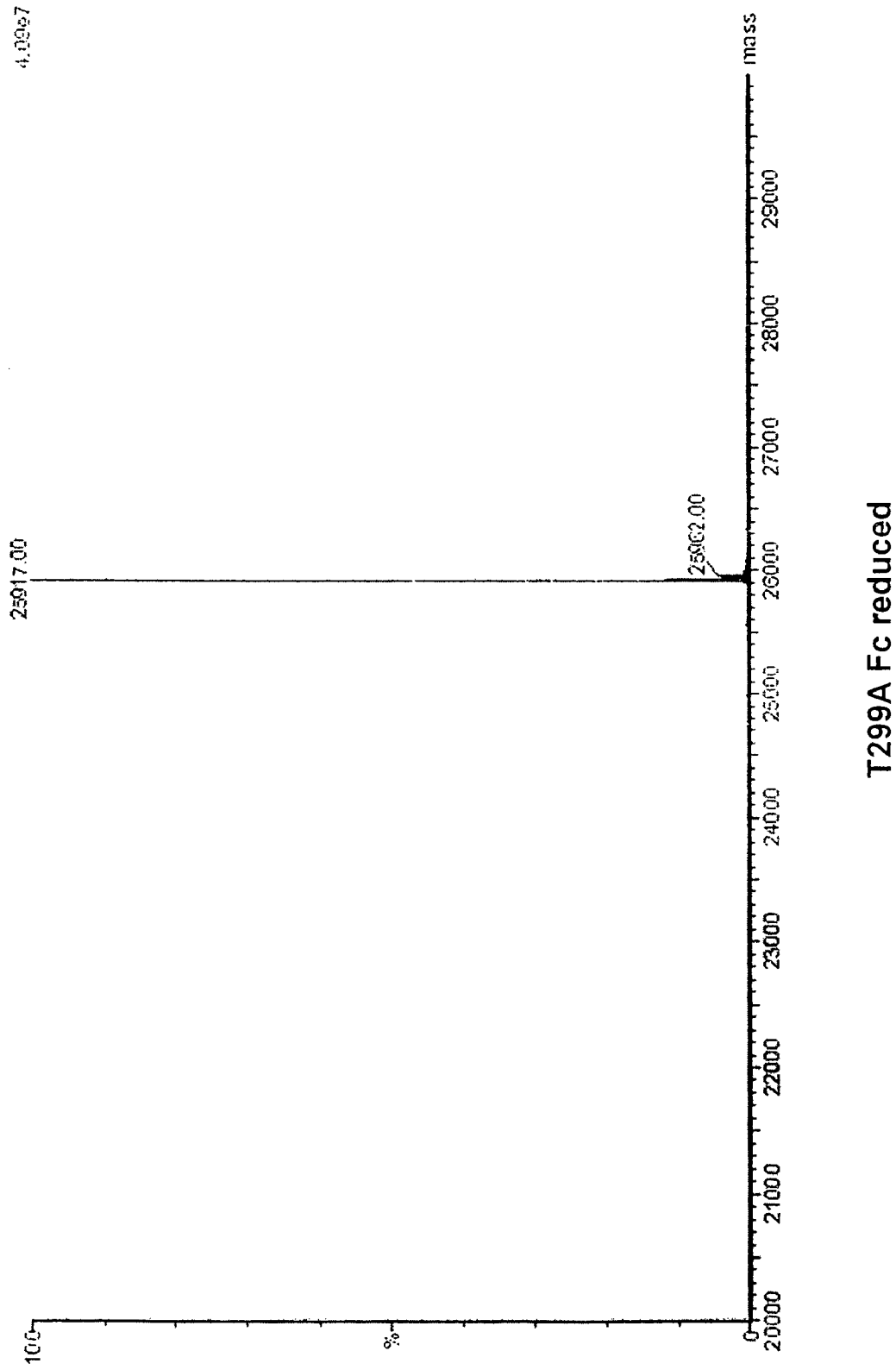
FIGS. 8-11 show mass spectroscopy histogram analyses of aglycosylated antibody variants having cysteine (T299C) or alanine (T299A) mutations under reducing and non-reducing conditions. The mass spectroscopy data shows that under non-reducing conditions the T299C antibody variant has added mass due to the formation of a cysteine adduct coupled to the cysteine at position 299 but that such an adduct does not form when an alanine is present (i.e., T299A).
Figure 9:
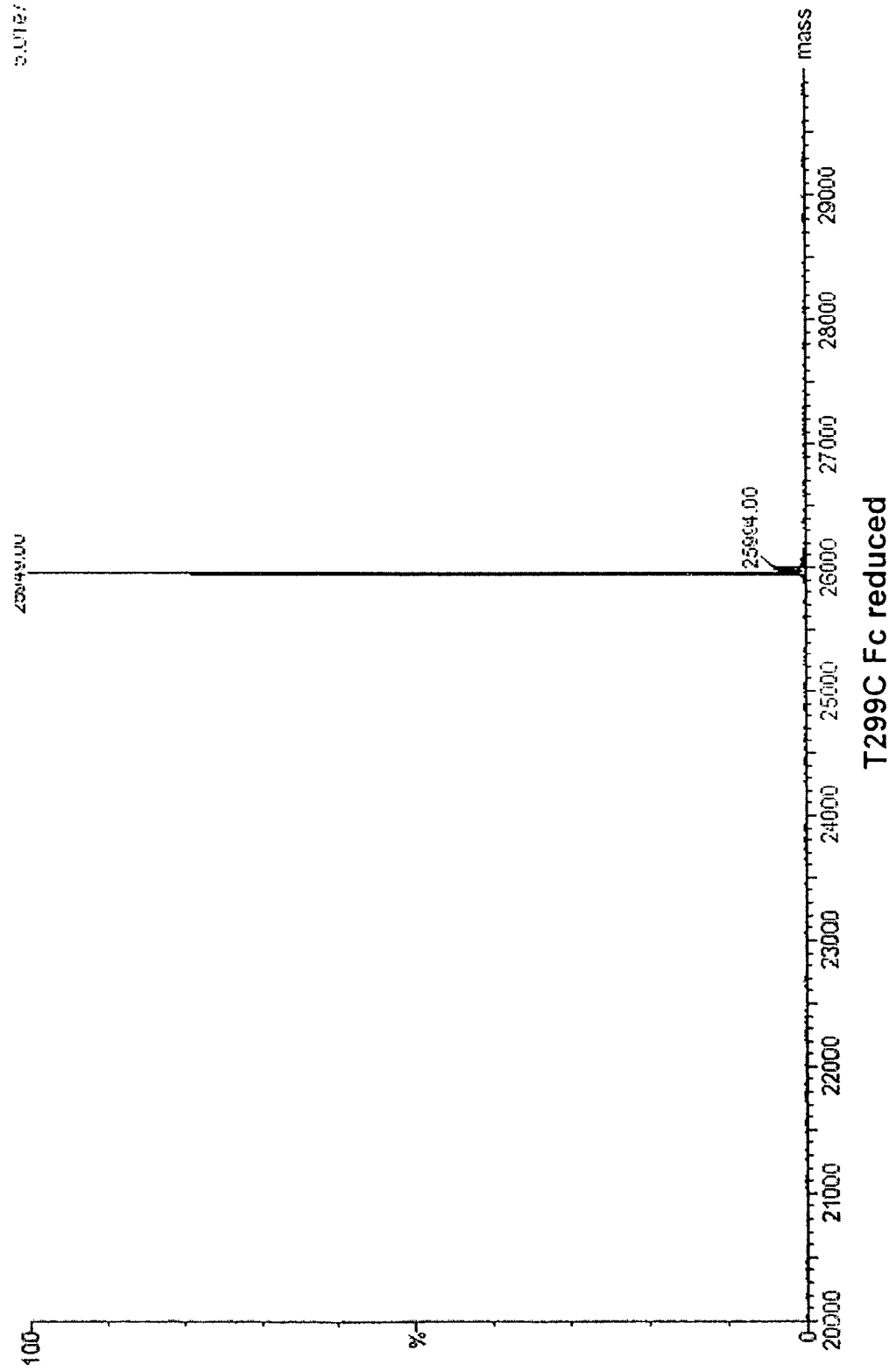
Figure 10:
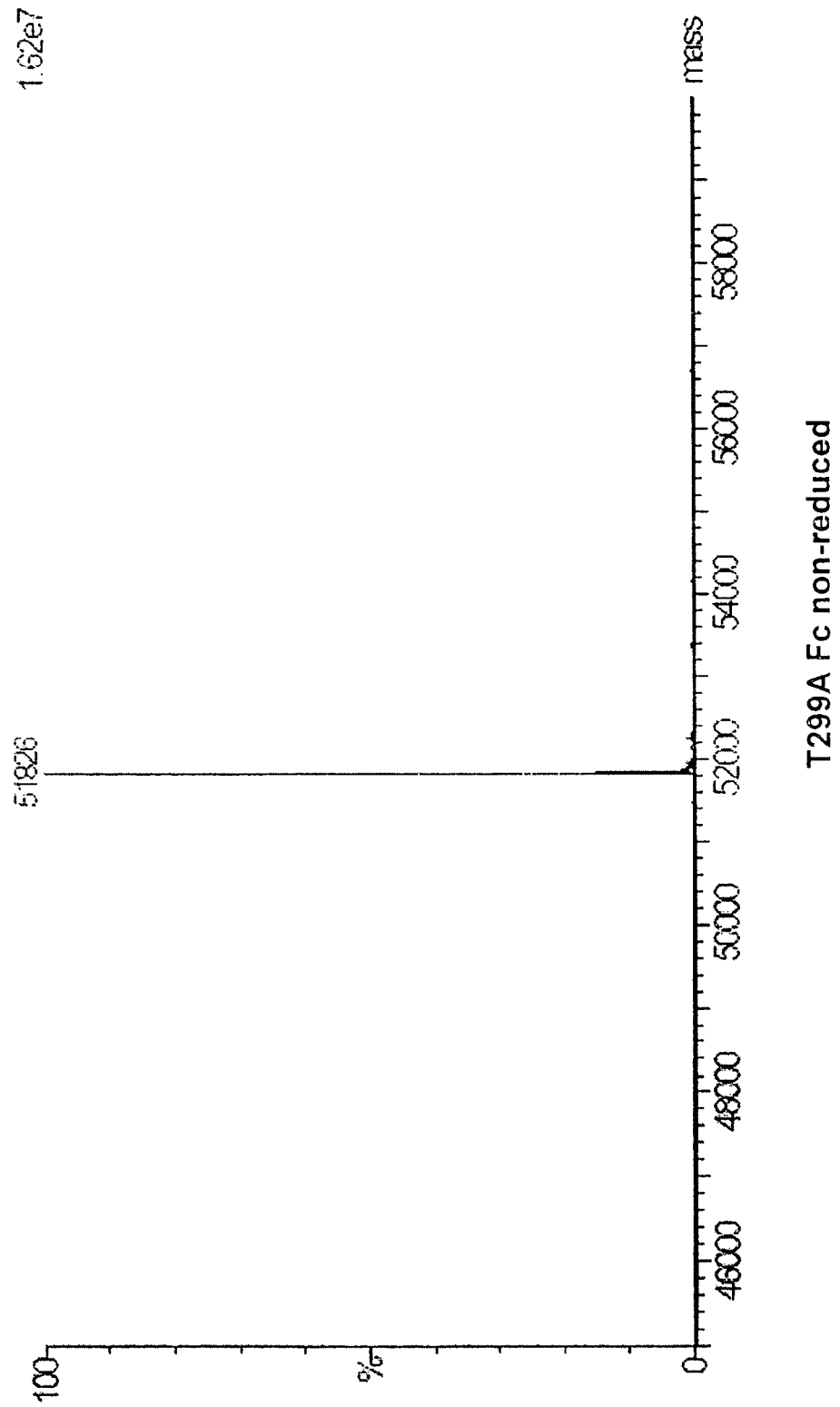
Figure 11:
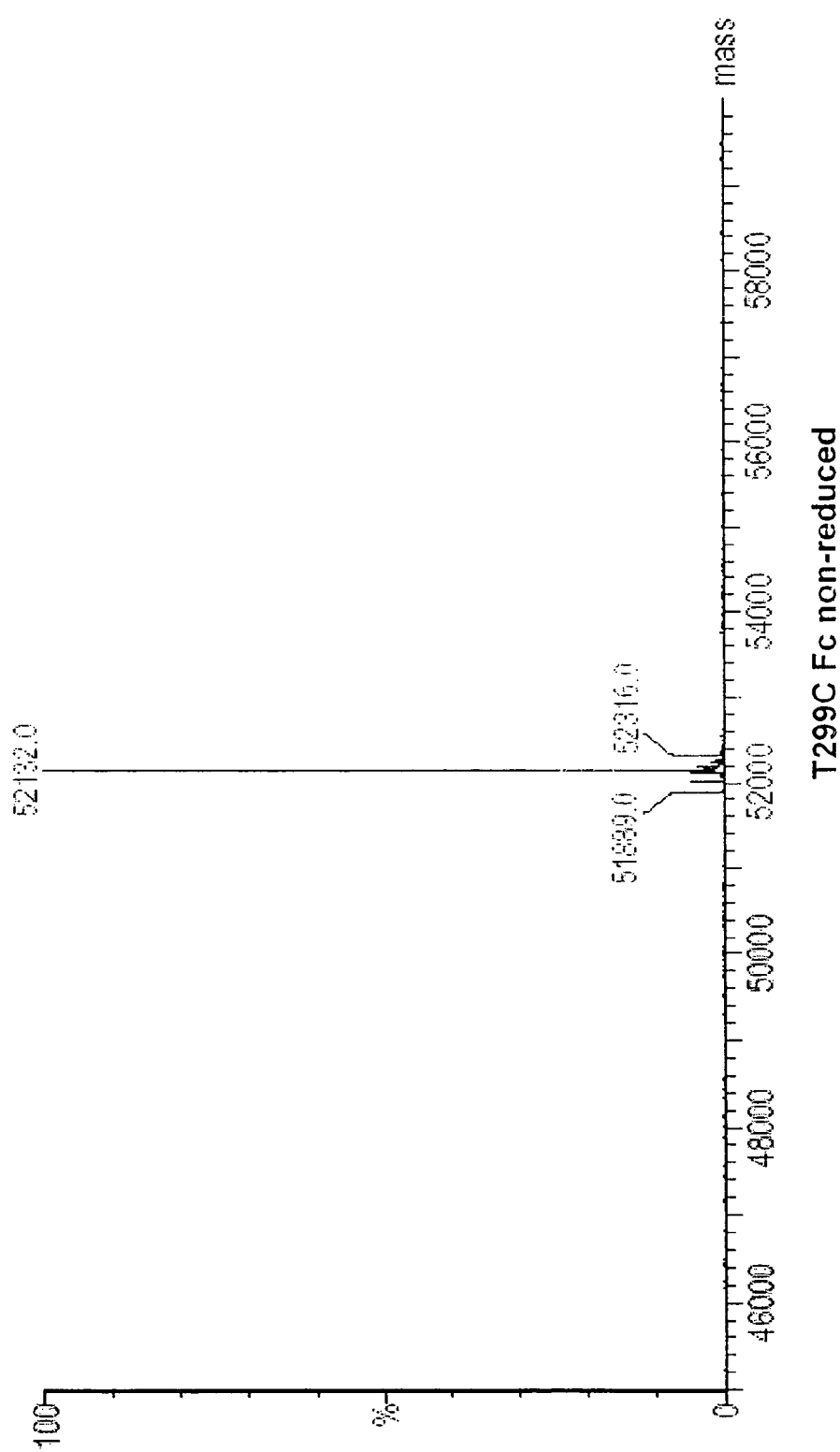

Briefly, to reduce the test proteins, 200 μL of the 0.94 mg/mL T299A and T299C Fc antibody variant preparations were treated with 4 μL of 500 mM EDTA, pH 8 (final concentration 10 mM) and 10 μL of 100 mM TCEP (final concentration 5 mM) for 3 hours at room temperature. The reduced proteins were dialyzed against PBS over four days with five changes at 1:1000 volume ratios. Aliquots (5 μL) of the protein preparations were then treated with 5 μL of 5 mM PEG-maleimide (5,000 mw) under non-denaturing conditions for 1 h and then prepared for SDS-PAGE by the addition of 5 μL of 4× Laemmli SDS-PAGE sample buffer contained 100 mM DTT. Only the T299C antibody variant was observed to have a PEG adduct (FIG. 7).

Corroboration that the T299C cysteine had formed a cystine disulfide bond was obtained by attempting to react the Fc with the thiol-specific modifying reagent, PEG-maleimide. Under denaturing (6.4 M urea, 2% SDS), but non-reducing conditions, no reaction occurred with the PEG-maleimide. Under reducing conditions the T299C variant did react with the PEG-maleimide, yielding a larger product than the T299A variant, indicating the presence of the extra cysteine (FIG. 3).

Accordingly, it was concluded that the alteration of the first amino acid proximal to a glycosylation motif capable of inhibiting the glycosylation of the antibody at a second amino acid residue, when altered to a cysteine residue, also provided for an efficient and reliable pegylation residue.

Example 4

Methods for Determining Altered Effector Function of Aglycosylated Antibodies

The following example describes assays for determining the altered effector function of the aglycosylated antibodies of the invention.

The effector function of the aglycosylated variant antibodies of the invention were characterized by their ability to bind an antigen and also bind an Fc receptor or a complement molecule such as C1q. In particular, the FcγR binding affinities were measured with assays based on the ability of the antibody to form a "bridge" between the CD154 antigen and a cell bearing an Fc receptor. The C1q binding affinity was measured based on the ability of the antibody to form a "bridge" between the CD154 antigen and C1q (FIGS. 14-15).

Briefly, the FcγR bridging assay was performed by coating 96 well Maxisorb ELISA plates (Nalge-Nunc Rochester, N.Y., USA) with recombinant soluble human CD154 ligand (i.e., at a concentration of 1 μg/ml overnight at 4° C. in PBS; Karpusas, Hsu et al. 1995). Titrations of glycosylated or aglycosylated forms of anti-CD154 antibody (hu5c8) were then bound to CD154 for 30 minutes at 37° C., the plates were then washed, and the binding of fluorescently labeled U937 ($CD64^+$) cells was measured. The U937 cells were grown in RPMI medium with 10% FBS, 10 mM HEPES, L-glutamine, and penicillin/streptomycin, split 1:2, and activated for one day prior to the assay with 1000 units/ml of IFNγ to increase Fc receptor (FcγRI) expression.

In another variation of the assay, the ability of the antibodies of the invention to bind to, or rather, fail to bind, to yet another Fc receptor, in particular, FcγRIII (CD16) was performed using the above bridging assay against fluorescently labeled human T cells (Jurkat cells) transfected with a CD16 expression construct. The ligand was produced by a monolayer of CD154-expressing Chinese Hamster Ovary (CHO) cells grown in 96 well tissue culture plates (Corning Life Sciences Acton, Mass., USA). The $CHO\text{-}CD154^+$ cells were seeded into 96 well plates at $1\times10^5$ cells/ml and grown to confluency in $\alpha^-$MEM with 10% dialyzed FBS, 100 nM methotrexate, L-glutamine, and penicillin/streptomycin (Gibco-BRL Rockville, Md., USA). The CD16+Jurkat cells were grown in RPMI with 10% FBS, 400 μg/ml Geneticin, 10 mM HEPES, sodium pyruvate, L-glutamine, and penicillin/streptomycin (Gibco-BRL) and split 1:2 one day prior to performing the assay.

In the assays for both receptors, the Fc receptor-bearing cells were labeled with 2',7'-bis-(2-carboxyethyl)-5-(and -6)-carboxyfluorescein acetoxymethyl ester (BCECF-AM) (Molecular Probes Eugene, Oreg., USA) for 20 minutes at 37° C. After washing to remove excess label, $1 \times 10^5$ of the labeled cells were incubated in the assay for 30 minutes at 37° C. Unbound FcγR positive cells were removed by washing several times and plates were read on a microplate reader (Cytofluor 2350 Fluorescent Microplate Reader, Millipore Corporation Bedford, Mass., USA) at an excitation wavelength of 485 nm and an emission wavelength of 530 nm.

Figure 12:
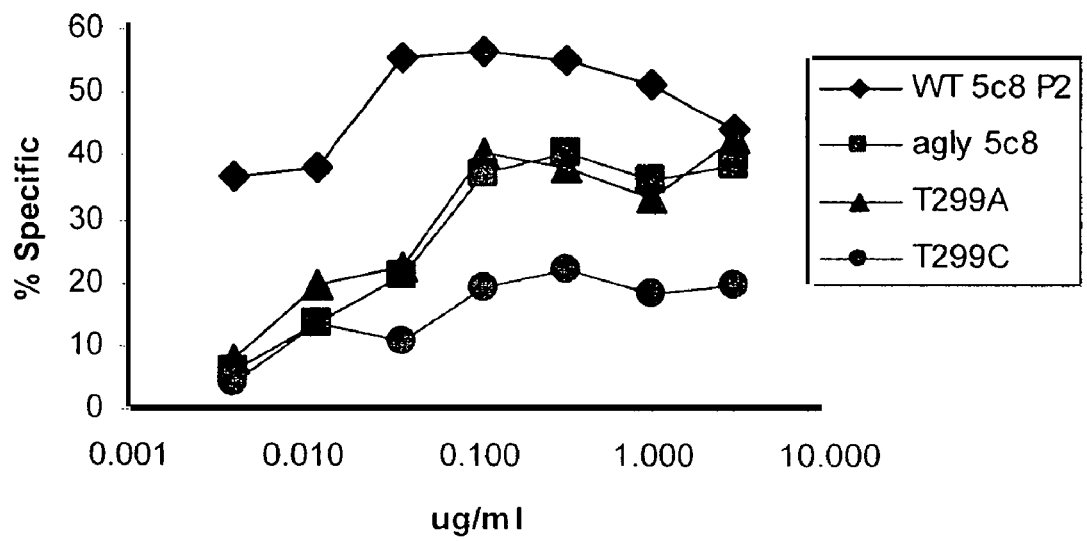
FIG. 12 shows the decreased effector function of the aglycosylated antibody IgG1 variants of the invention as a function of FcγRI (upper panel) or FcγRIII (lower) binding. The T299C variant, which is both aglycosylated and modified by a cysteine adduct, has less effector function (FcγRI binding) as compared to merely aglycosylated antibodies (upper panel).
Figure 12:
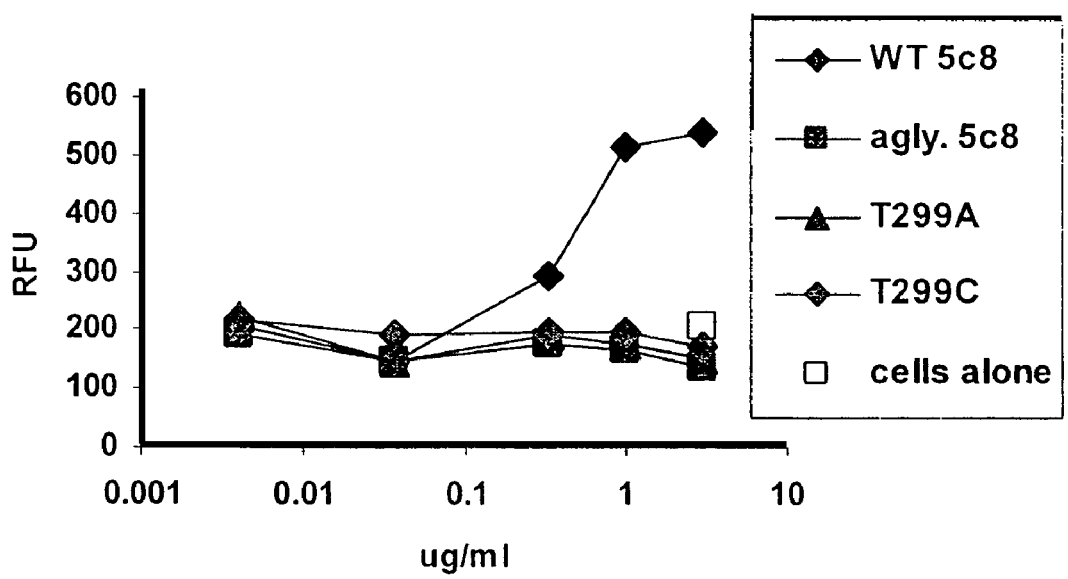
Figure 13:
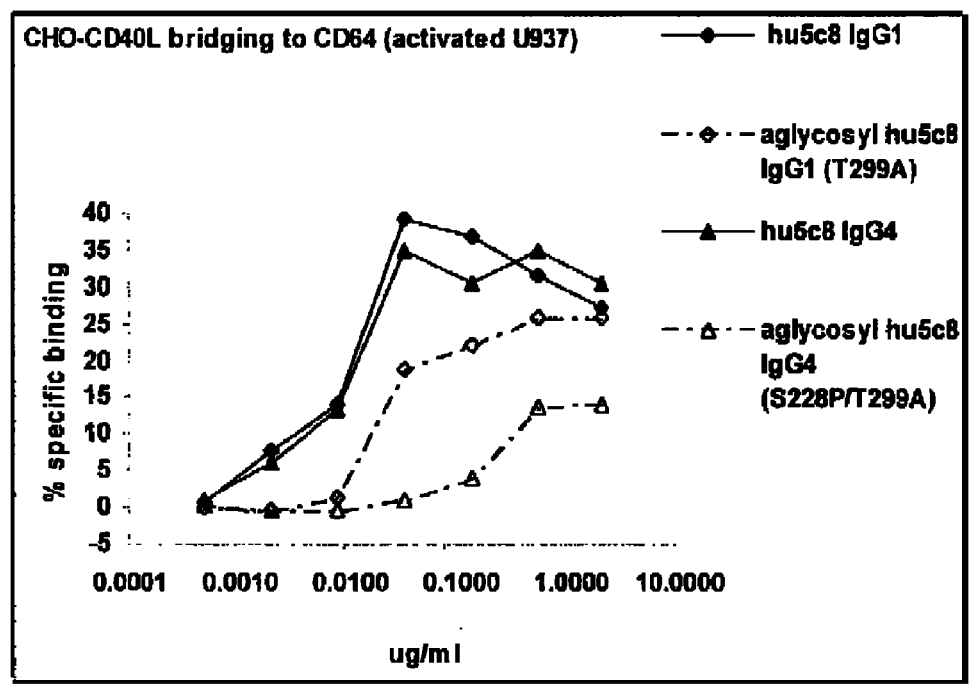
FIG. 13 shows the decreased effector function of the aglycosylated antibody IgG4 variant of the invention as a function of FcγRI (upper panel) or FcγRIII (lower) binding. The T299A IgG4 variant has less effector function (FcγRI binding) as compared to the aglycosylated IgG1 form.
Figure 13:
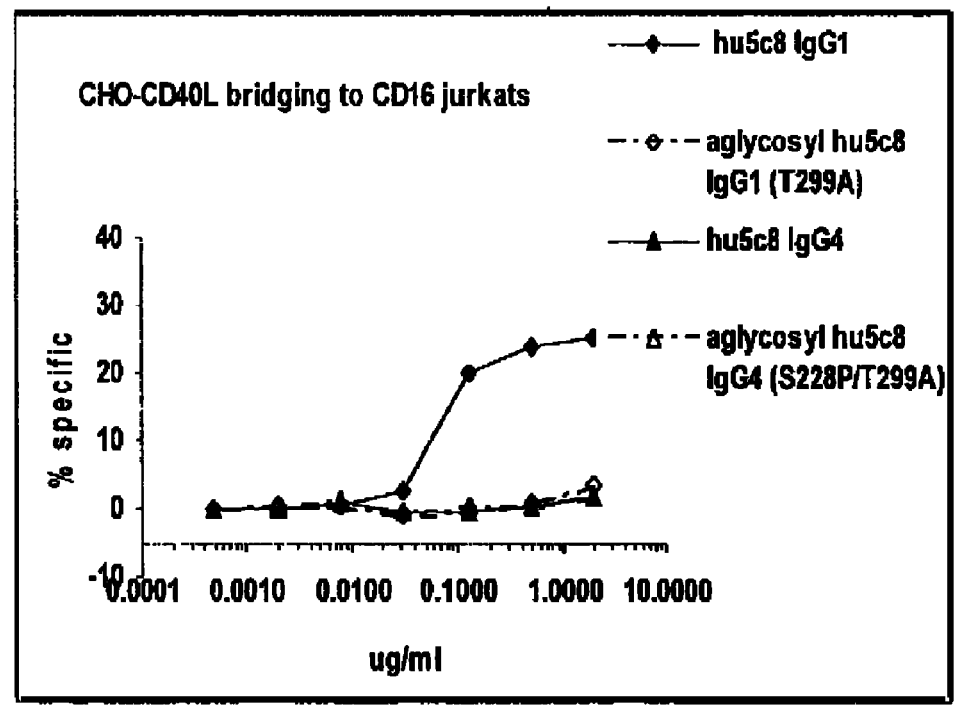

In each bridging assay, a reduced effector function of the aglycosylated IgG1 antibody variants of the invention as a function of FcγRI (upper panel) or FcγRIII (lower) binding was observed (FIGS. 12-13). In particular, the T299C variant, which is both aglycosylated and capable of forming a cysteine adduct was observed to have less effector function (FcγRI binding) as compared to merely aglycosylated antibodies (FIG. 12 upper panel). The aglycosyl IgG4 T299A antibody variant was also found to have exceptionally low binding to FcRγI, lower than the IgG1 T299A variant. This was not expected since the glycosylated IgG1 and IgG4 antibodies show similar binding in this assay (FIG. 13).

The C1q binding assay was performed by coating 96 well Maxisorb ELISA plates (Nalge-Nunc Rochester, N.Y., USA) with 50 μl recombinant soluble human CD154 ligand (Karpusas et al. Structure, 15; 3(12):1426 (1995) at 10 μg/ml overnight at 4° C. in PBS. The wells were aspirated and washed three times with wash buffer (PBS, 0.05% Tween 20) and blocked for $\geq$1 h with 200 μl/well of block/diluent buffer (0.1 M $Na_2HPO_4$, pH 7, 0.1 M NaCl, 0.05% Tween 20, 0.1% gelatin). The antibody to be tested was diluted in block/diluent buffer starting at 15 μg/ml with 3-fold dilutions. 50 μl were added per well, and the plates incubated for 2 h at room temperature. After aspirating and washing as above, 50 μl/well of 2 μg/ml of Sigma human C1q (C0660) diluted in block/diluent buffer was added and incubated for 1.5 h at room temperature. After aspirating and washing as above, 50 μl/well of sheep anti C1q (Serotec AHP033), diluted 3,560-fold in block/diluent buffer, was added. After incubation for 1 h at room temperature, the wells were aspirated and washed as above. 50 μl/well of donkey anti-sheep IgG HRP conjugate (Jackson ImmunoResearch 713-035-147) diluted to 1:10,000 in block/diluent was then added, and the wells incubated for 1 h at room temperature. After aspirating and washing as above, 100 μl TMB substrate (420 μM TMB, 0.004% $H_2O_2$ in 0.1 M sodium acetate/citric acid buffer, pH 4.9) was added and incubated for 2 min before the reaction was stopped with 100 μl 2 N sulfuric acid. The absorbance was read at 450 nm with a Softmax PRO instrument, and Softmax software was used to determine the relative binding affinity (C value) with a 4-parameter fit.

Figure 14:
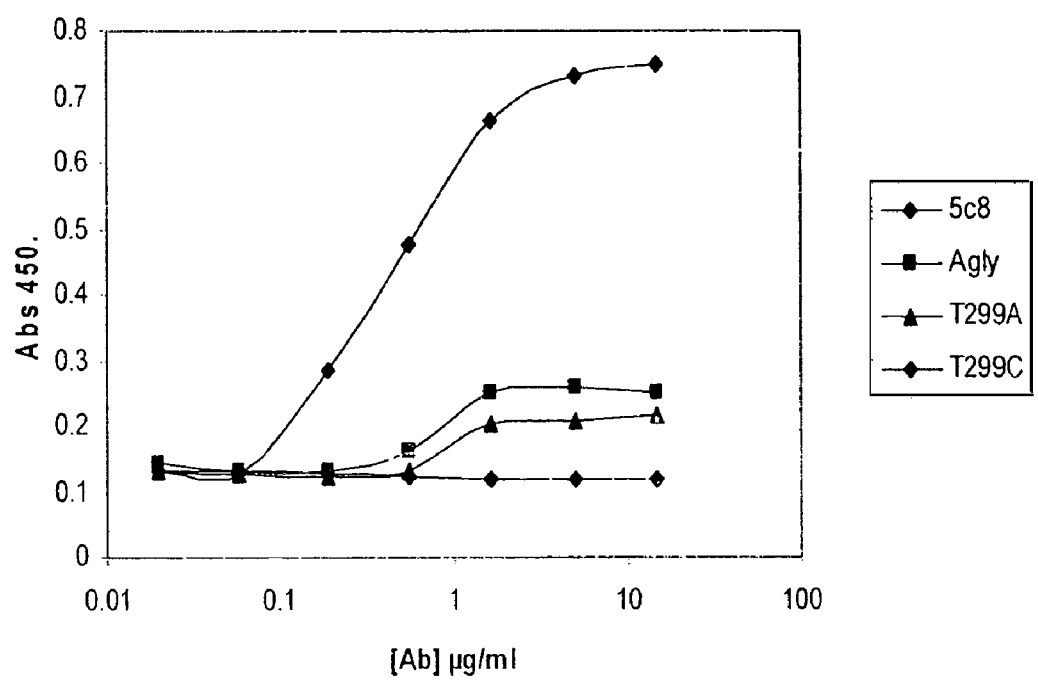
FIG. 14 shows the decreased effector function of the aglycosyl IgG1 antibody (i.e., hu5c8) as a function of binding to the complement protein C1q. The T299C variant, which is both aglycosylated and modified by a cysteine adduct, has less effector function (i.e., C1q binding) as compared to the aglycosylated only form.
Figure 15:
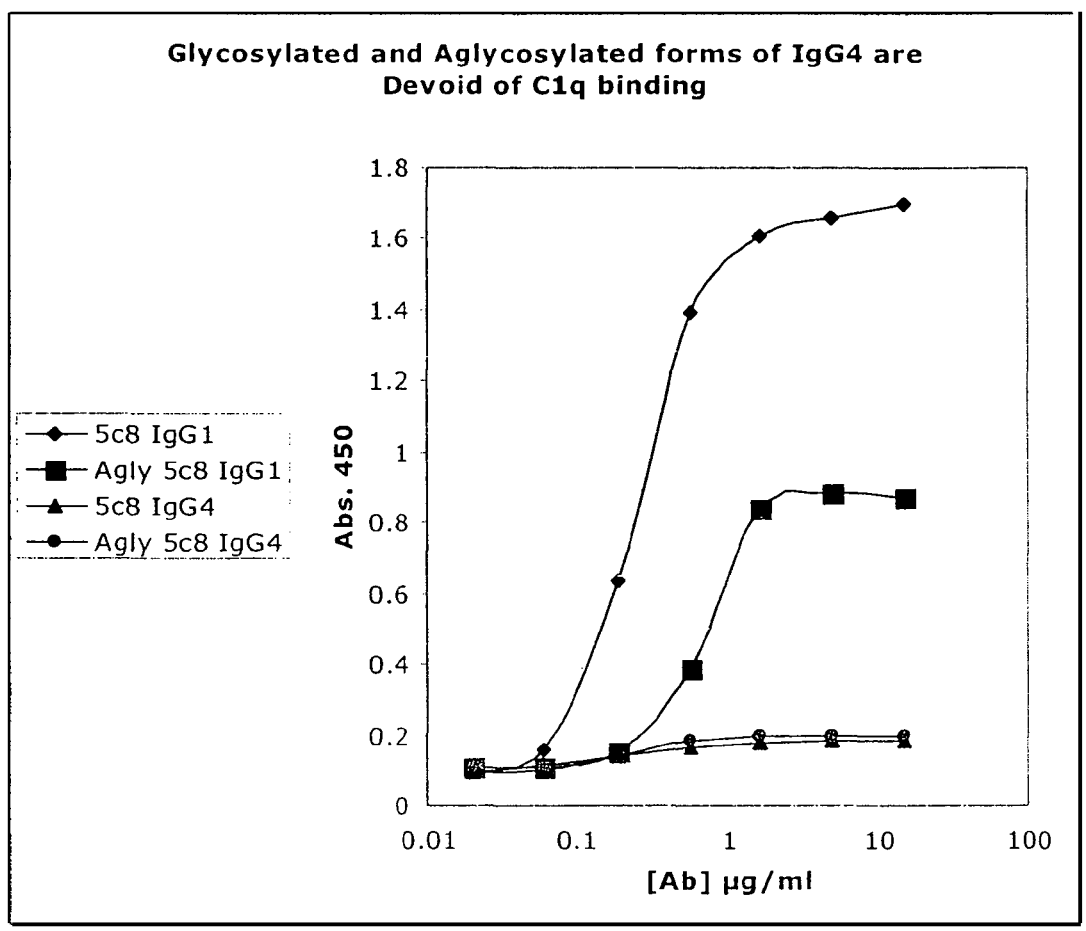
FIG. 15 shows the decreased effector function of the aglycosyl IgG4 antibody (i.e., hu5c8) as a function of binding to the complement protein C1q. The T299A IgG4 variant has less effector function (i.e., C1q binding) as compared to the aglycosylated IgG1 variant.

As shown in FIGS. 14-15, the T299C mutant had a C1q binding affinity that was not only below the hu5c8 antibody but below that of the aglycosylated N297Q and T299A variants, which indicates that the mutation to cysteine was unexpectedly beneficial. The IgG4 T299A mutant showed no binding to C1q, similarly to the aglycosylated IgG4.

Accordingly, it was concluded that the alteration of a first amino acid proximal to a glycosylation motif inhibited the glycosylation of the antibody at a second amino acid residue, and when the first amino acid was a cysteine residue, the antibody had more reduced effector function. In addition, inhibition of glycosylation of an antibody of the IgG4 subtype had a more profound affect on FcγRI binding than expected.

EQUIVALENTS

For one skilled in the art, using no more than routine experimentation, there are many equivalents to the specific embodiments of the invention described herein. Such equivalents are intended to be encompassed by the following claims.

The invention claimed is:

1. A variant polypeptide of a parent polypeptide comprising an Fc region, wherein the Fc region of the variant polypeptide comprises a modified first amino acid residue at T299 of the Fc region according to the Kabat numbering system of IgG immunoglobulins, the modified first amino acid residue having a side chain chemistry selected from the group consisting of a side chain chemistry comprising a cysteine thiol, a side chain chemistry of sufficient steric bulk such that the polypeptide displays reduced effector function, and a side chain chemistry of sufficient electrostatic charge such that the polypeptide displays reduced effector function, and a second amino acid residue at N297 of the Fc region according to the Kabat numbering system of IgG immunoglobulins, the second amino acid having reduced glycosylation, wherein the variant polypeptide has reduced effector function as compared to the parent polypeptide.

2. The variant polypeptide of claim 1, wherein the side chain chemistry of the modified first amino acid residue comprises a cysteine thiol.

3. The variant polypeptide of claim 1, wherein the side chain chemistry is of sufficient steric bulk such that the polypeptide displays reduced effector function.

4. The variant polypeptide of claim 3, wherein the side chain chemistry of sufficient steric bulk is that of an amino acid residue selected from the group consisting of Phe, Trp, His, Glu, Gln, Arg, Lys, Met, and Tyr.

5. The variant polypeptide of claim 1, wherein the side chain chemistry is of sufficient electrostatic charge such that the variant polypeptide displays reduced effector function.

6. The variant polypeptide of claim 5, wherein the side chain chemistry is that of an amino acid residue selected from the group consisting of Asp, Glu, Lys, Arg, and His.

7. The variant polypeptide of claim 1, wherein the reduced effector function is reduced binding to an Fc receptor (FcR).

8. The variant polypeptide of claim 7, wherein the binding is reduced by a factor selected from the group consisting of about 1-fold, about 2-fold, about 3-fold, about 4-fold, about 5-fold, about 6-fold, about 7-fold, about 8-fold, about 9-fold, about 10-fold, about 15-fold, about 50-fold, and about 100-fold.

9. The variant polypeptide of claim 7, wherein the Fc receptor (FcR) is selected from the group consisting of FcγRI, FcγRII, and FcγRIII.

10. The variant polypeptide of claim 1, wherein the reduced effector function is reduced binding to a complement protein.

11. The variant polypeptide of claim 10, wherein the complement protein is C1q.

12. The variant polypeptide of claim 10, wherein the reduced binding to a complement protein is by a factor selected from the group consisting of about 1-fold, about 2-fold, about 3-fold, about 4-fold, about 5-fold, about 6-fold, about 7-fold, about 8-fold, about 9-fold, about 10-fold, and about 15-fold.

13. The polypeptide of claim 1, wherein the first amino acid residue is modified by substitution by a replacement amino acid.

14. The variant polypeptide of claim 13, wherein the replacement amino acid is a non-traditional amino acid residue.

15. The variant polypeptide of claim 1, wherein the first amino acid residue is capable of being linked to a functional moiety.

16. The variant polypeptide of claim 15, wherein the functional moiety is selected from the group consisting of a blocking moiety, a detectable moiety, a diagnostic moiety, and a therapeutic moiety.

17. The variant polypeptide of claim 16, wherein the blocking moiety is selected from the group consisting of a cysteine adduct, mixed disulfide, polyethylene glycol, and polyethylene glycol maleimide.

18. The variant polypeptide of claim 16, wherein the detectable moiety is selected from the group consisting of a fluorescent moiety and isotopic moiety.

19. The variant polypeptide of claim 16, wherein the diagnostic agent is capable of revealing the presence of a disease or disorder.

20. The variant polypeptide of claim 16, wherein the therapeutic moiety is selected from the group consisting of an anti-inflammatory agent, an anticancer agent, an anti-neurodegenerative agent, and an anti-infective agent.

21. A variant polypeptide of a parent polypeptide comprising an IgG1 Fc region, wherein the Fc region of the variant polypeptide comprises an amino acid at position 299 which differs from the amino acid at position 299 of the parent polypeptide, wherein the amino acid at position 299 of the parent polypeptide is threonine and the amino acid at position 299 of the variant polypeptide is selected from the group consisting of alanine, asparagine, glycine, tyrosine, cysteine, histidine, glutamic acid, aspartic acid, lysine, arginine, isolucine, leucine, methionine, phenylalanine, proline, tryptophan, and valine, and wherein the variant polypeptide comprises an amino acid at position 297 of the Fc region having reduced glycosylation and displays reduced effector function as compared to the parent polypeptide.

22. The variant polypeptide of claim 21, wherein the amino acid at position 299 is a cysteine.

23. The variant polypeptide of claim 1, wherein the polypeptide is pegylated at the modified first amino acid residue.

24. The variant polypeptide of claim 2, wherein the polypeptide is pegylated with PEG-maleimide.

25. The variant polypeptide of claim 1, wherein the modified first amino acid residue is a cysteine residue modified by a cysteine or mixed disulfide adduct.

26. The variant polypeptide of claim 1, wherein the polypeptide is an antibody variant.

27. The variant polypeptide of claim 1, wherein the Fc region is obtained from an antibody of an isotype selected from the group consisting of IgG1, IgG2, IgG3, and IgG4.

28. The variant polypeptide of claim 1, wherein the polypeptide binds to an antigen selected from the group consisting of a ligand, cytokine, receptor, cell surface antigen, and cancer cell antigen.

29. The polypeptide of claim 21, wherein the amino acid at position 299 is an alanine.

30. A composition comprising the variant polypeptide of claim 29 in a suitable pharmaceutical carrier.

31. An antibody variant of a parent antibody, wherein the antibody variant comprises an Fc region comprising a replacement amino acid substituted for the threonine at position 299 of the Fc region according to the Kabat numbering system for IgG immunoglobulins, the substituted amino acid residue having a side chain chemistry selected from the group consisting of a side chain chemistry comprising a cysteine thiol, a side chain chemistry of sufficient steric bulk such that the polypeptide displays reduced effector function, and a side chain chemistry of sufficient electrostatic charge such that the polypeptide displays reduced effector function and a second amino acid residue at N297 of the Fc region according to the Kabat numbering system for IgG immunoglobulins, the second amino acid residue having reduced glycosylation as compared to the parent antibody.

32. The antibody variant of claim 31, which has reduced effector function.

33. A varaint antibody of a parent antibody comprising an IgG1 Fc region, wherein the Fc region of the variant antibody comprises an amino acid at position 299 which differs from the amino acid at position 299 of the parent antibody, wherein the amino acid threonine at position 299 of the parent antibody is threonine and the amino acid at position 299 of the variant antibody is selected from the group consisting of alanine, asparagine, glycine, tyrosine, cysteine, histidine, glutamic acid, aspartic acid, lysine, arginine, isolucine, leucine, methionine, phenylalanine, proline, tryptophan, and valine, and wherein the variant antibody comprises an amino acid at position 297 of the Fc region having reduced glycosylation and displays reduced effector function as compared to the parent polypeptide.

34. The antibody variant of claim 31, wherein the Fc region is from an IgG1 antibody.

35. The antibody variant of claim 33, wherein the replacement amino acid residue at position 299 is an alanine.

36. The antibody variant of claim 33, wherein the replacement amino acid residue at position 299 is a cysteine.

37. The antibody variant of claim 31, wherein the Fc region is from an IgG4 antibody.

38. The antibody variant of claim 37, wherein the replacement amino acid at position 299 is a cysteine.

39. The antibody variant of claim 37, wherein the Fc region further comprises an amino acid at position 228 which differs from the amino acid at position 228 of the parent antibody, wherein the amino acid at position 228 of the parent antibody is a serine and the amino acid at position 228 of the variant antibody is a proline.

40. The antibody variant of claim 37, wherein the amino acid at position 299 is alanine.

41. The antibody variant of claim 33, wherein the amino acid at position 299 is asparagine.

42. The antibody variant of claim 37, wherein the amino acid at position 299 is asparagine.

43. The antibody variant of claim 33, wherein the amino acid at position 299 is glycine.

44. The antibody variant of claim 37, wherein the amino acid at position 299 is glycine.

45. The antibody variant of claim 33, wherein the amino acid at position 299 is tyrosine.

46. The antibody variant of claim 37, wherein the amino acid at position 299 is tyrosine.

47. The antibody variant of claim 33, wherein the amino acid at position 299 is histadine.

48. The antibody variant of claim 37, wherein the amino acid at position 299 is histadine.

49. The antibody variant of claim 33, wherein the amino acid at position 299 is glutamic acid.

50. The antibody variant of claim 37, wherein the amino acid at position 299 is glutamic acid.

51. The antibody variant of claim 33, wherein the amino acid at position 299 is aspartic acid.

52. The antibody variant of claim 37, wherein the amino acid at position 299 is aspartic acid.

53. The antibody variant of claim 33, wherein the amino acid at position 299 is lysine.

54. The antibody variant of claim 37, wherein the amino acid at position 299 is lysine.

55. The antibody variant of claim 33, wherein the amino acid at position 299 is arginine.

56. The antibody variant of claim 37, wherein the amino acid at position 299 is arginine.

57. The antibody variant of claim 33, wherein the amino acid at position 299 is isoleucine.

58. The antibody variant of claim 37, wherein the the amino acid at position 299 is isoleucine.

59. The antibody variant of claim 33, wherein the amino acid at position 299 is leucine.

60. The antibody variant of claim 37, wherein the amino acid at position 299 is leucine.

61. The antibody variant of claim 33, wherein the amino acid at position 299 is methionine.

62. The antibody variant of claim 37, wherein the amino acid at position 299 is methionine.

63. The antibody variant of claim 33, wherein the amino acid at position 299 is phenylalanine.

64. The antibody variant of claim 37, wherein the amino acid at position 299 is phenylalanine.

65. The antibody variant of claim 33, the amino acid at position 299 is proline.

66. The antibody variant of claim 37, wherein the amino acid at position 299 is proline.

67. The antibody variant of claim 33, wherein the amino acid at position 299 is tryptophan.

68. The antibody variant of claim 37, wherein the amino acid at position 299 is tryptophan.

69. The antibody variant of claim 33, wherein the amino acid at position 299 is valine.

70. The antibody variant of claim 37, wherein the amino acid at position 299 is valine.

71. The variant polypeptide of claim 21, wherein the amino acid at position 299 is asparagine.

72. The variant polypeptide of claim 21, wherein the amino acid at position 299 is glycine.

73. The variant polypeptide of claim 21, wherein the amino acid at position 299 is tyrosine.

74. The variant polypeptide of claim 21, wherein the amino acid at position 299 is histadine.

75. The variant polypeptide of claim 21, wherein the amino acid at position 299 is glutamic acid.

76. The variant polypeptide of claim 21, wherein the amino acid at position 299 is aspartic acid.

77. The variant polypeptide of claim 21, wherein the amino acid at position 299 is a lysine.

78. The variant polypeptide of claim 21, wherein the amino acid at position 299 is an arginine.

79. The variant polypeptide of claim 21, wherein the amino acid at position 299 is isoleucine.

80. The variant polypeptide of claim 21, wherein the amino acid at position 299 is leucine.

81. The variant polypeptide of claim 21, wherein the amino acid at position 299 is methionine.

82. The variant polypeptide of claim 21, wherein the amino acid at position 299 is phenylalanine.

83. The variant polypeptide of claim 21, wherein the amino acid at position 299 is proline.

84. The variant polypeptide of claim 21, wherein the amino acid at position 299 is tryptophan.

85. The variant polypeptide of claim 21, wherein the amino acid at position 299 is valine.

86. A composition comprising the antibody variant of claim 35 in a suitable pharmaceutical carrier.

87. A variant polypeptide of a parent polypeptide comprising an IgG 1 Fc region, wherein the Fc region of the variant polypeptide comprises an amino acid at position 299 which differs from the amino acid at position 299 of the parent polypeptide, wherein the amino acid at position 299 of the parent polypeptide is threonine and the amino acid at position 299 of the variant polypeptide is an alanine, and wherein the variant polypeptide comprises an amino acid at position 297 of the Fc region having reduced glycosylation and displays reduced effector function as compared to the parent polypeptide.

88. A variant polypeptide of a parent polypeptide comprising an IgG4 Fc region, wherein the Fc region of the variant polypeptide comprises an amino acid at position 299 which differs from the amino acid at position 299 of the parent polypeptide, wherein the amino acid at position 299 of the parent polypeptide is threonine and the amino acid at position 299 of the variant polypeptide is an alanine, and wherein the variant polypeptide comprises an amino acid at position 297 of the Fc region having reduced glycosylation and displays reduced effector function as compared to the parent polypeptide.

* * * * *

SEQUENCE LISTING

```
<160> NUMBER OF SEQ ID NOS: 12

<210> SEQ ID NO 1
<211> LENGTH: 1404
<212> TYPE: DNA
<213> ORGANISM: Homo sapiens

<400> SEQUENCE: 1
atggactgga cctggagggt cttctgcttg ctggctgtag caccaggtgc ccactcccag      60
gtccaactgg tgcagtcagg ggctgaagtg gtgaagcctg ggcttcagt  gaagttgtcc     120 tgcaaggctt ctggctacat cttcaccagt tattatatgt actgggtgaa gcaggcgccc     180
ggacaaggcc ttgagtggat tggagagatt aatcctagca atggtgatac taacttcaat     240
gagaagttca agagtaaggc cacactgact gtagacaaat ccgccagcac agcatacatg     300
gagctcagca gcctgaggtc tgaggacact gcggtctatt actgtacaag atcggacggt     360
agaaatgata tggactcctg gggccaaggg accctggtca ccgtctcctc agcctccacc     420
aagggcccat cggtcttccc cctggcaccc tcctccaaga gcacctctgg ggcacagcg      480 gccctgggct gcctggtcaa ggactacttc cccgaaccgt gacggtgtc  gtggaactca     540 ggcgccctga ccagcggcgt gcacaccttc ccggctgtcc tacagtcctc aggactctac     600
```

```
tccctcagca gcgtggtgac cgtgccctcc agcagcttgg gcacccagac ctacatctgc        660
aacgtgaatc acaagcccag caacaccaag gtggacaaga agttgagcc caaatcttgt         720 gacaagactc acacatgccc accgtgccca gcacctgaac tcctgggggg accgtcagtc        780
ttcctcttcc ccccaaaacc caaggacacc ctcatgatct cccggacccc tgaggtcaca        840
tgcgtggtgg tggacgtgag ccacgaagac cctgaggtca agttcaactg gtacgtggac        900
ggcgtggagg tgcataatgc caagacaaag ccgcgggagg agcagtacaa cagcacgtac        960
cgtgtggtca gcgtcctcac cgtcctgcac caggactggc tgaatggcaa ggagtacaag       1020
tgcaaggtct ccaacaaagc cctcccagcc cccatcgaga aaaccatctc caaagccaaa       1080
gggcagcccc gagaaccaca ggtgtacacc ctgcccccat cccgggatga gctgaccaag       1140
aaccaggtca gcctgacctg cctggtcaaa ggcttctatc ccagcgacat cgccgtggag       1200
tgggagagca atgggcagcc ggagaacaac tacaagacca cgcctcccgt gttggactcc       1260
gacggctcct tcttcctcta cagcaagctc accgtggaca agagcaggtg gcagcagggg       1320
aacgtcttct catgctccgt gatgcatgag gctctgcaca accactacac gcagaagagc       1380
ctctccctgt ctcccgggaa atga                                              1404
```

<210> SEQ ID NO 2
<211> LENGTH: 467
<212> TYPE: PRT
<213> ORGANISM: Homo sapiens

<400> SEQUENCE: 2

```
Met Asp Trp Thr Trp Arg Val Phe Cys Leu Leu Ala Val Ala Pro Gly
 1               5                  10                  15

Ala His Ser Gln Val Gln Leu Val Gln Ser Gly Ala Glu Val Val Lys
            20                  25                  30

Pro Gly Ala Ser Val Lys Leu Ser Cys Lys Ala Ser Gly Tyr Ile Phe
        35                  40                  45

Thr Ser Tyr Tyr Met Tyr Trp Val Lys Gln Ala Pro Gly Gln Gly Leu
    50                  55                  60

Glu Trp Ile Gly Glu Ile Asn Pro Ser Asn Gly Asp Thr Asn Phe Asn
65                  70                  75                  80

Glu Lys Phe Lys Ser Lys Ala Thr Leu Thr Val Asp Lys Ser Ala Ser
                85                  90                  95

Thr Ala Tyr Met Glu Leu Ser Ser Leu Arg Ser Glu Asp Thr Ala Val
            100                 105                 110

Tyr Tyr Cys Thr Arg Ser Asp Gly Arg Asn Asp Met Asp Ser Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220
```

```
Lys Pro Ser Asn Thr Lys Val Asp Lys Val Glu Pro Lys Ser Cys
225                 230                 235                 240

Asp Lys Thr His Thr Cys Pro Pro Cys Pro Ala Pro Glu Leu Leu Gly
            245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Asp Glu Leu Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465

<210> SEQ ID NO 3
<211> LENGTH: 717
<212> TYPE: DNA
<213> ORGANISM: Homo sapiens

<400> SEQUENCE: 3
atggagacag acacactcct gttatgggtg ctgctgctct gggttccagg ttccactggt     60
gacattgtac tgacacagtc tcctgctacc ttatctgtat ctccgggaga gagggccacc    120
atctcatgca gggccagcca acgtgtcagt tcatctacct atagttatat gcactggtac    180
caacagaaac caggacagcc acccaaactc ctcatcaagt atgcatccaa cctagaatct    240
ggggtccctg ccaggttcag tggcagtggg tctgggactg acttcaccct caccatctct    300
tctgtggagc cggaggattt tgcaacatat tactgtcagc acagttggga gattcctccg    360
acgttcggtg agggaccaa gctggagatc aaacgaactg tggctgcacc atctgtcttc    420
atcttcccgc catctgatga gcagttgaaa tctggaactg cctctgttgt gtgcctgctg    480
aataacttct atcccagaga ggccaaagta cagtggaagg tggataacgc cctccaatcg    540
ggtaactccc aggagagtgt cacagagcag gacagcaagg acagcaccta cagcctcagc    600
agcaccctga cgctgagcaa agcagactac gagaaacaca agtctacgc ctgcgaagtc    660 acccatcagg gcctgagctc gcccgtcaca aagagcttca caggggaga gtgttag       717
```

<210> SEQ ID NO 4
<211> LENGTH: 238
<212> TYPE: PRT
<213> ORGANISM: Homo sapiens

<400> SEQUENCE: 4

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Thr Leu Ser
            20                  25                  30

Val Ser Pro Gly Glu Arg Ala Thr Ile Ser Cys Arg Ala Ser Gln Arg
        35                  40                  45

Val Ser Ser Ser Thr Tyr Ser Tyr Met His Trp Tyr Gln Gln Lys Pro
    50                  55                  60

Gly Gln Pro Pro Lys Leu Leu Ile Lys Tyr Ala Ser Asn Leu Glu Ser
65                  70                  75                  80

Gly Val Pro Ala Arg Phe Ser Gly Ser Gly Ser Gly Thr Asp Phe Thr
                85                  90                  95

Leu Thr Ile Ser Ser Val Glu Pro Glu Asp Phe Ala Thr Tyr Tyr Cys
            100                 105                 110

Gln His Ser Trp Glu Ile Pro Pro Thr Phe Gly Gly Gly Thr Lys Leu
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 5
<211> LENGTH: 756
<212> TYPE: DNA
<213> ORGANISM: Homo sapiens

<400> SEQUENCE: 5
atgaagctcc ccgtcaggct tctcgtgctc atgttctgga ttccggcgtc gtcaagtgag      60
cccaaatcta gtgacaagac tcacacatgc ccaccgtgcc cagcacctga actcctgggg     120
ggaccgtcag tcttcctctt ccccccaaaa cccaaggaca cctcatgat ctcccggacc      180 cctgaggtca catgcgtggt ggtggacgtg agccacgaag accctgaggt caagttcaac     240
tggtacgtgg acggcgtgga ggtgcataat gccaagacaa agccgcggga ggagcagtac     300
aacagcacgt accgtgtggt cagcgtcctc accgtcctgc accaggactg gctgaatggc     360
aaggagtaca agtgcaaggt ctccaacaaa gccctcccag cccccatcga gaaaaccatc     420
tccaaagcca aagggcagcc ccgagaacca caggtgtaca ccctgccccc atcccgcgat     480
gagctgacca agaaccaggt cagcctgacc tgcctggtca aaggcttcta tcccagcgac     540

```
atcgccgtgg agtgggagag caatgggcag ccggagaaca actacaagac cacgcctccc    600
gtgttggact ccgacggctc cttcttcctc tacagcaagc tcaccgtgga caagagcagg    660
tggcagcagg ggaacgtctt ctcatgctcc gtgatgcatg aggctctgca caaccactac    720
acgcagaaga gcctctccct gtctcccggg aaatga                              756
```

<210> SEQ ID NO 6
<211> LENGTH: 251
<212> TYPE: PRT
<213> ORGANISM: Homo sapiens

<400> SEQUENCE: 6

```
Met Lys Leu Pro Val Arg Leu Leu Val Leu Met Phe Trp Ile Pro Ala
1               5                   10                  15

Ser Ser Ser Glu Pro Lys Ser Ser Asp Lys Thr His Thr Cys Pro Pro
            20                  25                  30

Cys Pro Ala Pro Glu Leu Leu Gly Gly Pro Ser Val Phe Leu Phe Pro
        35                  40                  45

Pro Lys Pro Lys Asp Thr Leu Met Ile Ser Arg Thr Pro Glu Val Thr
    50                  55                  60

Cys Val Val Val Asp Val Ser His Glu Asp Pro Glu Val Lys Phe Asn
65                  70                  75                  80

Trp Tyr Val Asp Gly Val Glu Val His Asn Ala Lys Thr Lys Pro Arg
                85                  90                  95

Glu Glu Gln Tyr Asn Ser Thr Tyr Arg Val Val Ser Val Leu Thr Val
            100                 105                 110

Leu His Gln Asp Trp Leu Asn Gly Lys Glu Tyr Lys Cys Lys Val Ser
        115                 120                 125

Asn Lys Ala Leu Pro Ala Pro Ile Glu Lys Thr Ile Ser Lys Ala Lys
    130                 135                 140

Gly Gln Pro Arg Glu Pro Gln Val Tyr Thr Leu Pro Pro Ser Arg Asp
145                 150                 155                 160

Glu Leu Thr Lys Asn Gln Val Ser Leu Thr Cys Leu Val Lys Gly Phe
                165                 170                 175

Tyr Pro Ser Asp Ile Ala Val Glu Trp Glu Ser Asn Gly Gln Pro Glu
            180                 185                 190

Asn Asn Tyr Lys Thr Thr Pro Pro Val Leu Asp Ser Asp Gly Ser Phe
        195                 200                 205

Phe Leu Tyr Ser Lys Leu Thr Val Asp Lys Ser Arg Trp Gln Gln Gly
    210                 215                 220

Asn Val Phe Ser Cys Ser Val Met His Glu Ala Leu His Asn His Tyr
225                 230                 235                 240

Thr Gln Lys Ser Leu Ser Leu Ser Pro Gly Lys
                245                 250
```

<210> SEQ ID NO 7
<211> LENGTH: 1335
<212> TYPE: DNA
<213> ORGANISM: Homo sapiens

<400> SEQUENCE: 7

```
caggtccaac tggtgcagtc aggggctgaa gtggtgaagc tggggcttc agtgaagttg    60 tcctgcaagg cttctggcta catcttcacc agttattata tgtactgggt gaagcaggcg   120
cccggacaag gccttgagtg gattggagag attaatccta gcaatggtga tactaacttc   180
```

-continued

```
aatgagaagt tcaagagtaa ggccacactg actgtagaca atccgccag cacagcatac    240 atggagctca gcagcctgag gtctgaggac actgcggtct attactgtac aagatcggac    300
ggtagaaatg atatggactc ctggggccaa gggaccctgg tcaccgtctc ctcagcttcc    360
accaagggcc catccgtctt ccccctggcg ccctgctcca gatctacctc cgagagcaca    420
gccgccctgg gctgcctggt caaggactac ttccccgaac cggtgacggt gtcgtggaac    480
tcaggcgccc tgaccagcgg cgtgcacacc ttcccggctg tcctacagtc ctcaggactc    540
tactccctca gcagcgtggt gaccgtgccc tccagcagct tgggcacgaa gacctacacc    600
tgcaacgtag atcacaagcc cagcaacacc aaggtggaca gagagttga gtccaaatat    660 ggtccccat gcccatcatg cccagcacct gagttcctgg ggggaccatc agtcttcctg    720
ttccccccaa acccaagga cactctcatg atctcccgga cccctgaggt cacgtgcgtg    780
gtggtggacg tgagccagga agaccccgag gtccagttca actggtacgt ggatggcgtg    840
gaggtgcata atgccaagac aaagccgcgg gaggagcagt tcaacagcac gtaccgtgtg    900
gtcagcgtcc tcaccgtcct gcaccaggac tggctgaacg gcaaggagta caagtgcaag    960
gtctccaaca aaggcctccc gtcctccatc gagaaaacca tctccaaagc caagggcag   1020 cccccgagagc acaagtgta caccctgccc ccatcccagg aggagatgac caagaaccag   1080
gtcagcctga cctgcctggt caaaggcttc taccccagcg acatcgccgt ggagtgggag   1140
agcaatgggc agccggagaa caactacaag accacgcctc ccgtcctcga ttccgacggc   1200
tccttcttcc tctacagcag gctaaccgtg gacaagagca ggtggcagga ggggaatgtc   1260
ttctcatgct ccgtgatgca tgaggctctg cacaaccact acacacagaa gagcctctcc   1320
ctgtctctgg gttga                                                    1335

<210> SEQ ID NO 8
<211> LENGTH: 444
<212> TYPE: PRT
<213> ORGANISM: Homo sapiens

<400> SEQUENCE: 8

Gln Val Gln Leu Val Gln Ser Gly Ala Glu Val Lys Pro Gly Ala
  1               5                  10                  15

Ser Val Lys Leu Ser Cys Lys Ala Ser Gly Tyr Ile Phe Thr Ser Tyr
              20                  25                  30

Tyr Met Tyr Trp Val Lys Gln Ala Pro Gly Gln Gly Leu Glu Trp Ile
          35                  40                  45

Gly Glu Ile Asn Pro Ser Asn Gly Asp Thr Asn Phe Asn Glu Lys Phe
      50                  55                  60

Lys Ser Lys Ala Thr Leu Thr Val Asp Lys Ser Ala Ser Thr Ala Tyr
 65                  70                  75                  80

Met Glu Leu Ser Ser Leu Arg Ser Glu Asp Thr Ala Val Tyr Tyr Cys
                  85                  90                  95

Thr Arg Ser Asp Gly Arg Asn Asp Met Asp Ser Trp Gly Gln Gly Thr
             100                 105                 110

Leu Val Thr Val Ser Ser Ala Ser Thr Lys Gly Pro Ser Val Phe Pro
         115                 120                 125

Leu Ala Pro Cys Ser Arg Ser Thr Ser Glu Ser Thr Ala Ala Leu Gly
     130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
```

```
                    165                 170                 175
Ser Ser Gly Leu Tyr Ser Leu Ser Val Val Thr Val Pro Ser Ser
                180                 185                 190

Ser Leu Gly Thr Lys Thr Tyr Thr Cys Asn Val Asp His Lys Pro Ser
            195                 200                 205

Asn Thr Lys Val Asp Lys Arg Val Glu Ser Lys Tyr Gly Pro Pro Cys
        210                 215                 220

Pro Ser Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly
        435                 440

<210> SEQ ID NO 9
<211> LENGTH: 1335
<212> TYPE: DNA
<213> ORGANISM: Homo sapiens

<400> SEQUENCE: 9
caggtccaac tggtgcagtc aggggctgaa gtggtgaagc tggggcttc  agtgaagttg      60 tcctgcaagg cttctggcta catcttcacc agtattata  tgtactgggt gaagcaggcg     120
cccggacaag gccttgagtg gattggagag attaatccta gcaatggtga ctactaactt     180
aatgagaagt tcaagagtaa ggccacactg actgtagaca atccgccag  cacagcatac     240 atggagctca gcagcctgag gtctgaggac actgcggtct attactgtac aagatcggac     300
ggtagaaatg atatggactc ctggggccaa gggaccctgg tcaccgtctc ctcagcttcc     360
accaagggcc catccgtctt ccccctggcg ccctgctcca gatctacctc cgagagcaca     420
gccgccctgg gctgcctggt caaggactac ttccccgaac cggtgacggt gtcgtggaac     480
tcaggcgccc tgaccagcgg cgtgcacacc ttcccggctg tcctacagtc ctcaggactc     540
```

-continued

```
tactccctca gcagcgtggt gaccgtgccc tccagcagct tgggcacgaa gacctacacc    600
tgcaacgtag atcacaagcc cagcaacacc aaggtggaca gagagttgaa gtccaaatat    660
ggtcccccat gcccaccgtg cccagcacct gagttcctgg ggggaccatc agtcttcctg    720
ttccccccaa aacccaagga cactctcatg atctcccgga cccctgaggt cacgtgcgtg    780
gtggtggacg tgagccagga agaccccgag gtccagttca actggtacgt ggatggcgtg    840
gaggtgcata atgccaagac aaagccgcgg gaggagcagt tcaacagcac gtaccgtgtg    900
gtcagcgtcc tcaccgtcct gcaccaggac tggctgaacg gcaaggagta caagtgcaag    960
gtctccaaca aaggcctccc gtcctccatc gagaaaacca tctccaaagc caagggcag   1020
ccccgagagc cacaagtgta caccctgccc ccatcccagg aggagatgac caagaaccag   1080
gtcagcctga cctgcctggt caaaggcttc taccccagcg acatcgccgt ggagtgggag   1140
agcaatgggc agccggagaa caactacaag accacgcctc ccgtcctcga ttccgacggc   1200
tccttcttcc tctacagcag gctaaccgtg gacaagagca ggtggcagga ggggaatgtc   1260
ttctcatgct ccgtgatgca tgaggctctg cacaaccact acacacagaa gagcctctcc   1320
ctgtctctgg gttga                                                    1335
```

<210> SEQ ID NO 10
<211> LENGTH: 444
<212> TYPE: PRT
<213> ORGANISM: Homo sapiens

<400> SEQUENCE: 10

```
Gln Val Gln Leu Val Gln Ser Gly Ala Glu Val Val Lys Pro Gly Ala
 1               5                  10                  15

Ser Val Lys Leu Ser Cys Lys Ala Ser Gly Tyr Ile Phe Thr Ser Tyr
            20                  25                  30

Tyr Met Tyr Trp Val Lys Gln Ala Pro Gly Gln Gly Leu Glu Trp Ile
        35                  40                  45

Gly Glu Ile Asn Pro Ser Asn Gly Asp Thr Asn Phe Asn Glu Lys Phe
    50                  55                  60

Lys Ser Lys Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Ser Asp Gly Arg Asn Asp Met Asp Ser Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
```

```
                225                 230                 235                 240
        Phe Pro Pro Lys Pro Lys Asp Thr Leu Met Ile Ser Arg Thr Pro Glu
                        245                 250                 255

Val Thr Cys Val Val Val Asp Val Ser Gln Glu Asp Pro Glu Val Gln
                    260                 265                 270

Phe Asn Trp Tyr Val Asp Gly Val Glu Val His Asn Ala Lys Thr Lys
                275                 280                 285

Pro Arg Glu Glu Gln Phe Asn Ser Thr Tyr Arg Val Val Ser Val Leu
            290                 295                 300

Thr Val Leu His Gln Asp Trp Leu Asn Gly Lys Glu Tyr Lys Cys Lys
        305                 310                 315                 320

Val Ser Asn Lys Gly Leu Pro Ser Ser Ile Glu Lys Thr Ile Ser Lys
                        325                 330                 335

Ala Lys Gly Gln Pro Arg Glu Pro Gln Val Tyr Thr Leu Pro Pro Ser
                    340                 345                 350

Gln Glu Glu Met Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
        385                 390                 395                 400

Ser Phe Phe Leu Tyr Ser Arg Leu Thr Val Asp Lys Ser Arg Trp Gln
                        405                 410                 415

Glu Gly Asn Val Phe Ser Cys Ser Val Met His Glu Ala Leu His Asn
                    420                 425                 430

His Tyr Thr Gln Lys Ser Leu Ser Leu Ser Leu Gly
                435                 440

<210> SEQ ID NO 11
<211> LENGTH: 1335
<212> TYPE: DNA
<213> ORGANISM: Homo sapiens

<400> SEQUENCE: 11
caggtccaac tggtgcagtc aggggctgaa gtggtgaagc tggggcttc  agtgaagttg       60 tcctgcaagg cttctggcta catcttcacc agttattata tgtactgggt gaagcaggcg      120
cccggacaag gccttgagtg gattggagag attaatccta gcaatggtga tactaacttc      180
aatgagaagt tcaagagtaa ggccacactg actgtagaca atccgccag  cacagcatac      240 atggagctca gcagcctgag gtctgaggac actgcggtct attactgtac aagatcggac      300
ggtagaaatg atatggactc tggggccaa  gggaccctgg tcaccgtctc ctcagcttcc      360
accaagggcc catccgtctt ccccctggcg ccctgctcca gatctacctc cgagagcaca      420
gccgccctgg gctgcctggt caaggactac ttccccgaac cggtgacggt cgtggaaac      480 tcaggcgccc tgaccagcgg cgtgcacacc ttcccggctg tcctacagtc ctcaggactc      540
tactccctca gcagcgtggt gaccgtgccc tccagcagct gggcacgaa  gacctacacc      600 tgcaacgtag atcacaagcc cagcaacacc aaggtggaca gagagttga  gtccaaatat      660 ggtccccat  gcccaccgtg cccagcacct gagttcctgg ggggaccatc agtcttcctg      720
ttccccccaa aacccaagga cactctcatg atctcccgga cccctgaggt cacgtgcgtg      780
gtggtggacg tgagccagga agaccccgag gtccagttca actggtacgt ggatggcgtg      840
gaggtgcata atgccaagac aaagccgcgg gaggagcagt tcaacagcgc gtaccgtgtg      900
```

-continued

```
gtcagcgtcc tcaccgtcct gcaccaggac tggctgaacg gcaaggagta caagtgcaag    960
gtctccaaca aaggcctccc gtcctccatc gagaaaacca tctccaaagc caagggcag    1020 ccccgagagc acaagtgta caccctgccc catcccagg aggagatgac caagaaccag    1080
gtcagcctga cctgctggt caaaggcttc taccccagcg acatcgccgt ggagtgggag    1140
agcaatgggc agccggagaa caactacaag accacgcctc ccgtcctcga ttccgacggc    1200
tccttcttcc tctacagcag gctaaccgtg gacaagagca ggtggcagga ggggaatgtc    1260
ttctcatgct ccgtgatgca tgaggctctg cacaaccact acacacagaa gagcctctcc    1320
ctgtctctgg gttga                                                    1335
```

<210> SEQ ID NO 12
<211> LENGTH: 444
<212> TYPE: PRT
<213> ORGANISM: Homo sapiens

<400> SEQUENCE: 12

```
Gln Val Gln Leu Val Gln Ser Gly Ala Glu Val Val Lys Pro Gly Ala
 1               5                  10                  15

Ser Val Lys Leu Ser Cys Lys Ala Ser Gly Tyr Ile Phe Thr Ser Tyr
            20                  25                  30

Tyr Met Tyr Trp Val Lys Gln Ala Pro Gly Gln Gly Leu Glu Trp Ile
        35                  40                  45

Gly Glu Ile Asn Pro Ser Asn Gly Asp Thr Asn Phe Asn Glu Lys Phe
    50                  55                  60

Lys Ser Lys Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Ser Asp Gly Arg Asn Asp Met Asp Ser Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Ala Tyr Arg Val Val Ser Val Leu
```

-continued

```
            290                 295                 300
Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
                340                 345                 350

Gln Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
                420                 425                 430

His Tyr Thr Gln Lys Ser Leu Ser Leu Ser Leu Gly
            435                 440
```